(12) United States Patent
Paknahad et al.

(10) Patent No.: US 12,426,801 B2
(45) Date of Patent: Sep. 30, 2025

(54) CONTACT-FREE BREATH ANALYSIS DEVICE AND METHOD

(71) Applicant: CANNABIX TECHNOLOGIES INC., Burnaby (CA)

(72) Inventors: Mohammad Paknahad, Vancouver (CA); Sagar Rajesh Mehta, Vancouver (CA); Daryoush Sahebjavaher, Vancouver (CA)

(73) Assignee: CANNABIX TECHNOLOGIES INC., Burnaby (CA)

( * ) Notice: Subject to any disclaimer, the term of this patent is extended or adjusted under 35 U.S.C. 154(b) by 0 days.

(21) Appl. No.: 18/729,658

(22) PCT Filed: Mar. 27, 2023

(86) PCT No.: PCT/CA2023/050409
§ 371 (c)(1),
(2) Date: Jul. 17, 2024

(87) PCT Pub. No.: WO2023/178454
PCT Pub. Date: Sep. 28, 2023

(65) Prior Publication Data
US 2024/0415408 A1      Dec. 19, 2024

Related U.S. Application Data

(60) Provisional application No. 63/323,953, filed on Mar. 25, 2022.

(51) Int. Cl.
*A61B 5/08*     (2006.01)
*A61B 5/00*     (2006.01)
*A61B 5/087*    (2006.01)
*A61B 5/097*    (2006.01)

(52) U.S. Cl.
CPC .............. *A61B 5/082* (2013.01); *A61B 5/087* (2013.01); *A61B 5/097* (2013.01); *A61B 5/6893* (2013.01); *A61B 2503/22* (2013.01)

(58) Field of Classification Search
None
See application file for complete search history.

(56) References Cited

U.S. PATENT DOCUMENTS

| | | | |
|---|---|---|---|
| 4,868,545 A | 9/1989 | Jones | |
| 6,795,775 B2 | 9/2004 | Traylor, III | |
| 7,603,886 B2 | 10/2009 | Stock | |
| 8,323,206 B2 | 12/2012 | Castrodale | |
| 9,192,324 B2 | 11/2015 | Phillips et al. | |

(Continued)

FOREIGN PATENT DOCUMENTS

| AU | 2020100588 A4 | 6/2020 |
|---|---|---|
| CA | 1337463 C | 10/1995 |

(Continued)

*Primary Examiner* — Jacqueline Cheng
*Assistant Examiner* — Samuel C Kim
(74) *Attorney, Agent, or Firm* — Viridant IP

(57) ABSTRACT

Apparatus and methods for contact-free breath analysis are provided. One aspect provides a pneumatic circuit that can be used for analyzing a contact-free breath sample or a breath sample provided through an inlet tube. Some aspects provide apparatus that can be incorporated into a rearview mirror or steering wheel of a vehicle, or used as a standalone unit.

19 Claims, 15 Drawing Sheets

(56) References Cited

U.S. PATENT DOCUMENTS

| | | |
|---|---|---|
| 9,366,665 B1 | 6/2016 | Granstam et al. |
| 9,562,883 B2 | 2/2017 | Knott et al. |
| 9,696,294 B2 | 7/2017 | Phillips |
| 10,226,201 B2 | 3/2019 | Ahmad et al. |
| 11,209,417 B2 | 12/2021 | Jameson et al. |
| 11,275,021 B2 | 3/2022 | Hunt et al. |
| 11,375,920 B2 | 7/2022 | Ratto et al. |
| 11,391,724 B2 | 7/2022 | Hok et al. |
| 11,399,737 B2 | 8/2022 | Ratto et al. |
| 11,426,096 B2 | 8/2022 | Hunt et al. |
| 11,474,096 B2 | 10/2022 | Rekow et al. |
| 11,609,225 B2 | 3/2023 | Willkomm et al. |
| 11,619,626 B2 | 4/2023 | Son |
| 11,977,086 B2 * | 5/2024 | Lynn .................. G01N 33/497 |
| 2003/0228702 A1 * | 12/2003 | Stock .................. A61B 5/097 436/132 |
| 2006/0195040 A1 | 8/2006 | Nason |
| 2007/0245801 A1 | 10/2007 | Stock |
| 2010/0081955 A1 * | 4/2010 | Wood, Jr. .............. A61B 5/097 600/532 |
| 2012/0310104 A1 * | 12/2012 | Van Kesteren ........ A61B 5/082 600/532 |
| 2013/0231871 A1 * | 9/2013 | Hok .................... G01N 33/497 702/19 |
| 2013/0305808 A1 | 11/2013 | Yoo |
| 2014/0276100 A1 | 9/2014 | Satterfield et al. |
| 2014/0297111 A1 * | 10/2014 | Takahashi .............. B60K 28/00 701/36 |
| 2015/0160190 A1 | 6/2015 | Ravishankar |
| 2015/0219620 A1 | 8/2015 | Hok |
| 2015/0362478 A1 | 12/2015 | Phillips |
| 2016/0022172 A1 | 1/2016 | Frandsen |
| 2018/0120278 A1 * | 5/2018 | Hoorfar ............. G01N 33/0031 |
| 2018/0315503 A1 | 11/2018 | Hunt et al. |
| 2019/0175065 A1 * | 6/2019 | Knestel .................. A61B 5/097 |
| 2019/0183418 A1 | 6/2019 | Hunt et al. |
| 2020/0000372 A1 * | 1/2020 | Saito ...................... A61B 5/097 |
| 2020/0225211 A1 * | 7/2020 | Willkomm ......... G01N 33/0008 |
| 2024/0049984 A1 | 2/2024 | Sullivan |

FOREIGN PATENT DOCUMENTS

| | | |
|---|---|---|
| WO | WO2006/086323 A1 | 8/2006 |
| WO | WO2011/143693 A1 | 11/2011 |
| WO | WO2012/099365 A3 | 12/2012 |
| WO | WO2017/062017 A1 | 4/2017 |

* cited by examiner

CONTACT-FREE BREATH ANALYSIS DEVICE AND METHOD

CROSS-REFERENCE TO RELATED APPLICATIONS

This application is a national stage entry of PCT patent application No. PCT/CA2023/050409 filed 27 Mar. 2023, which claims priority to, and the benefit of, U.S. provisional patent application No. 63/323,953 filed 25 Mar. 2022. Both of the foregoing applications are incorporated by reference herein in their entireties for all purposes.

TECHNICAL FIELD

Some embodiments relate to apparatus or methods for detecting the presence of substances in breath, for example alcohol, cannabis or other controlled substances. Some embodiments relate to apparatus for detecting the presence of substances in breath that are incorporated into a standard component of a vehicle or piece of machinery or equipment. Some embodiments relate to methods for detecting the presence of substances in breath using an apparatus incorporated into a standard component of a vehicle or piece of machinery or equipment.

BACKGROUND

There exist a variety of controlled substances such as alcohol, cannabis or other drugs that impair or interfere with the mental functions and response times of those who consume such substances. Authorities or employers may set maximum acceptable limits for the presence of such substances in order for people to be able to drive or operate vehicles, machinery or other heavy or hazardous equipment.

For example, public authorities have generally determined that, for alcohol, a maximum concentration of alcohol that may be present in order for a person to legally operate a motor vehicle on public roads is in the range of 0.05 blood alcohol content (BAC) (i.e. 50 milligrams of alcohol per 100 mL of blood). If a person has a higher concentration of alcohol in their blood, they are generally not able to safely operate a motor vehicle and are prohibited from driving on public roads.

Apparatus such as breathalyzers that can be used to detect the presence of controlled substances in breath are known. Such breathalyzers can be incorporated into a vehicle or piece of machinery or other equipment, for example to allow a subject to blow into the breathalyzer to verify sobriety prior to operating the vehicle or piece of machinery or other equipment. Some breathalyzers are connected with the vehicle or piece of equipment so that if the breathalyzer determines that the subject's breath contains at least one prohibited substance, the vehicle or piece of equipment will not turn on.

Such breathalyzers generally require that a subject's mouth contact a mouthpiece of the breathalyzer in order to provide a sample for analysis. For a variety of reasons (e.g. concern over limiting the spread of communicable diseases, higher levels of comfort for a user), it can in some cases be undesirable to use a mouthpiece in order to obtain a breath sample for analysis. However, contactless breath collection presents a greater challenge than using a mouthpiece to direct sample flow into a testing apparatus, as there is greater dilution of sample before the sample reaches a detection unit, and there is also the possibility for cross-contamination or cross-reactivity which can lead to false positives (for example if a user has sanitized their hands with an alcohol-based hand sanitizer, alcohol in vapour form from the hand sanitizer could become co-mingled with the user's breath in the process of providing a sample to a contactless apparatus).

Breath samples can also be used for numerous other purposes, for example to detect levels of other prohibited substances such as cannabis or narcotics in the bloodstream of a subject, to evaluate disease status or conditions, or so on.

There is a general desire for systems and methods that can facilitate the obtention of a breath sample for analysis without the subject making physical contact with the apparatus.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In some aspects, an apparatus for evaluating a concentration of a target analyte in a user's bloodstream using a breath sample is provided. The apparatus has first and second inlets for receiving a respective portion of the breath sample and directing the respective portion along first and second fluid flow paths, respectively, an analyte sensor in fluid communication with the first inlet along a sampling arm of the first fluid flow path, a first pressure sensor in fluid communication with the second inlet along the second fluid flow path, and a first pump positioned to draw a portion of the breath sample into the sampling arm of the first fluid flow path.

In some aspects, the apparatus further has a second pump positioned to draw a portion of the breath sample to the analyte sensor from the sampling arm. In some aspects, a selectivity channel is provided between the sampling arm and the analyte sensor. In some aspects, the selectivity channel is a microfluidic channel.

In some aspects, the first inlet is configured to receive a sample tube. In some aspects, a second pressure sensor is provided on the first fluid flow path. In some aspects, the fluid flow path has both a sampling arm and a regulating arm that are connected by a T-connector, and the second pressure sensor can be provided on the regulating arm while the second pump is provided on the sampling arm. In some such aspects, a one-way valve that allows only downstream flow of air can interpose the second pressure sensor and the T-connector. In some aspects, an exhaust can be provided at a downstream end of the sampling arm and the regulating arm.

In some aspects, a method of evaluating a concentration of a target analyte in a user's bloodstream is provided. A breath sample is received from the user in a contact-free manner and directed simultaneously through first and second fluid flow paths via first and second inlets. A first pressure sensor in fluid communication with the second inlet is used to activate a first pump positioned to draw a portion of the breath sample into a sampling arm of the first fluid flow path, and the concentration of the target analyte in the user's bloodstream is evaluated using an analyte sensor in fluid communication with the second fluid flow path.

In some aspects, the method further includes using the first pressure sensor to calculate a volume of the provided breath sample. In some aspects, the method further includes receiving a second breath sample from a second user via a sample tube coupled to the first inlet. In some aspects, the method further includes using a second pressure sensor disposed on the first fluid flow path to calculate a volume of the second breath sample. In some aspects, the first fluid flow path has a sampling arm and a regulating arm separated by a T-connector, and the regulating arm has a one-way valve that allows a breath sample to flow only in a downstream direction. In some aspects, when the system is used in a contact-free manner, the one-way valve prevents upstream flow of fluid through the regulating arm. In some aspects, the second pressure sensor is disposed on the regulating arm downstream of the one-way valve, and when the breath sample is provided through a sample tube, the method includes allowing the pressure of the user's breath sample to open the one-way valve.

In some aspects, the pneumatic circuit has a main fluid flow path with a first pump configured to draw a user's breath sample into the main fluid flow path. A secondary sample path is provided off the main fluid flow path, with an analyte sensor disposed therein. A second pump can be used to draw a portion of the user's breath sample into the sample path to allow detection by the analyte sensor. A selectivity channel, which can be a microfluidic channel, can be provided in the sample path upstream of the analyte sensor to help increase the selectivity of the system.

In some aspects, a pneumatic circuit as described in any of the above paragraphs can be incorporated into a component of a vehicle such as a rearview mirror or a steering wheel. In some aspects, a pneumatic circuit as described above can be provide as a standalone unit, for example in a cabinet-mounted housing or the like.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

As used herein, a reference to a vehicle, equipment or heavy machinery encompasses any type of apparatus that may be operated by a human. Non-limiting examples of vehicles, equipment or heavy machinery may include cars, trucks, SUVs, vans, recreational vehicles, commercial trucks, tractors, excavators, dumptrucks, equipment used in construction or resource extraction activities such as mining or oil and gas, manufacturing or other equipment in a factory or the like, and so on.

As used herein, a reference to an analyte includes any desired molecule of interest. In some embodiments, the analyte of interest is alcohol. However, in various embodiments, suitable sensors, or a plurality of different kinds of sensors, may be used to detect any one or more analytes of interest, e.g. delta-9-tetrahydrocannabinol (for which the permitted blood alcohol level is 5 ng/ml of blood), other prohibited substances such as narcotics, or the like, or levels of ammonia or biologic biomarkers indicative of a person's state of health or possible infection with a microorganism or the like.

Figure 1:
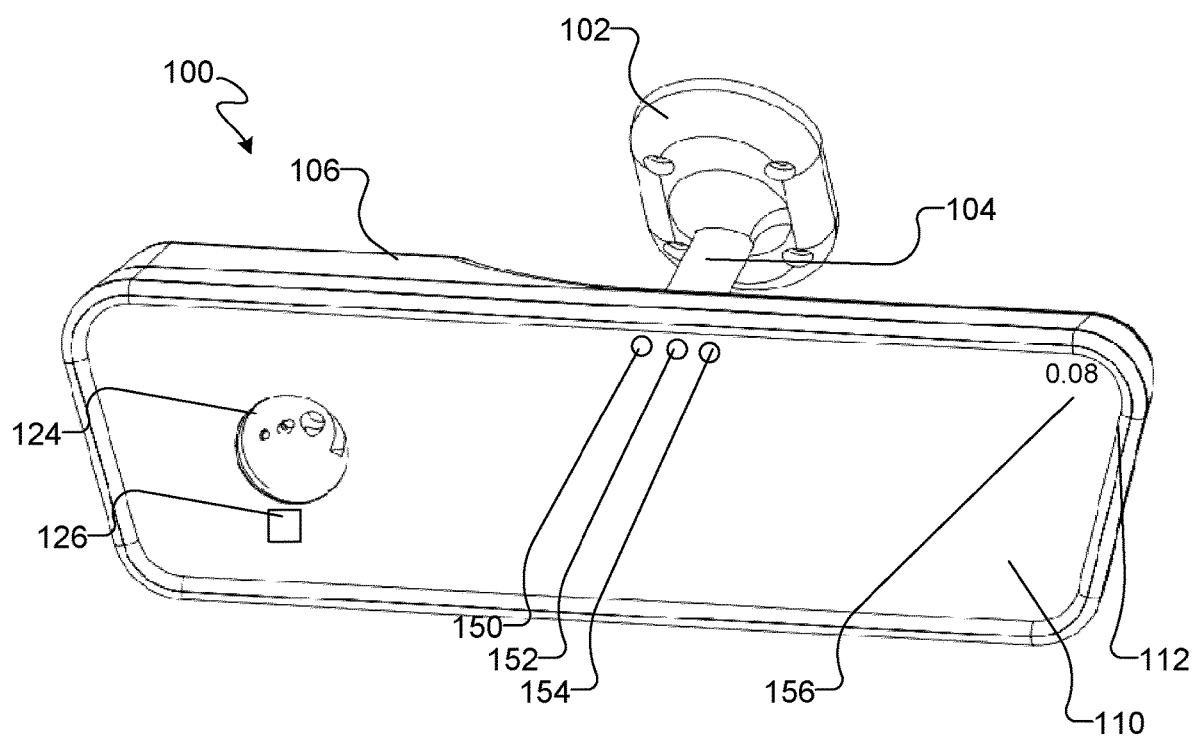
FIG. 1 shows an example embodiment of a contact-free breath analysis apparatus, incorporated as part of a rearview mirror of a vehicle.

With reference to FIG. 1, an example embodiment of a contact-free breath analysis apparatus 50 that is integrated into a standard component of a vehicle, namely a rearview mirror 100 of the vehicle, is illustrated. While in the illustrated embodiment contact-free breath analysis apparatus 50 is illustrated as being integrated with a rearview mirror, in alternative embodiments, contact-free breath analysis apparatus 50 could be integrated into any other desired component of a vehicle or piece of equipment, or provided adjacent to such components, in order to be used as described herein to detect substances from a breath sample in a contact-free manner.

In some embodiments in which apparatus 50 is integrated into a mirror or other surface on which condensation is visible, the visual feedback provided by the mirrored surface as described below can assist a user in properly positioning their lips to be able to provide a breath sample. Additionally, a mirror can be supplied as an external or easily replaceable component to the vehicle, making integrating apparatus 50 into the vehicle more straightforward than other embodiments in which apparatus 50 is integrated into an integral component of the vehicle (e.g. as a component of a dashboard), and/or making it easier to remove apparatus 50 for maintenance, calibration or the like. Moreover, a rearview mirror is one of the few components inside the cabin of a vehicle that is positioned approximately at a level of the driver's head, making rearview mirror 100 convenient for use by the driver. Further, power is supplied to the rearview mirror of the vehicle (e.g. for lights, internal communications systems contained within the rearview mirror, lighted overhead consoles etc.), so power can be readily supplied to apparatus 50.

Rearview mirror 100 is connected to the vehicle in any suitable manner, for example via a conventional base 102 connected to a connector arm 104. Rearview mirror 100 has a rear housing 106 and a front housing 108 that contains and supports the components further discussed below.

Figure 2:
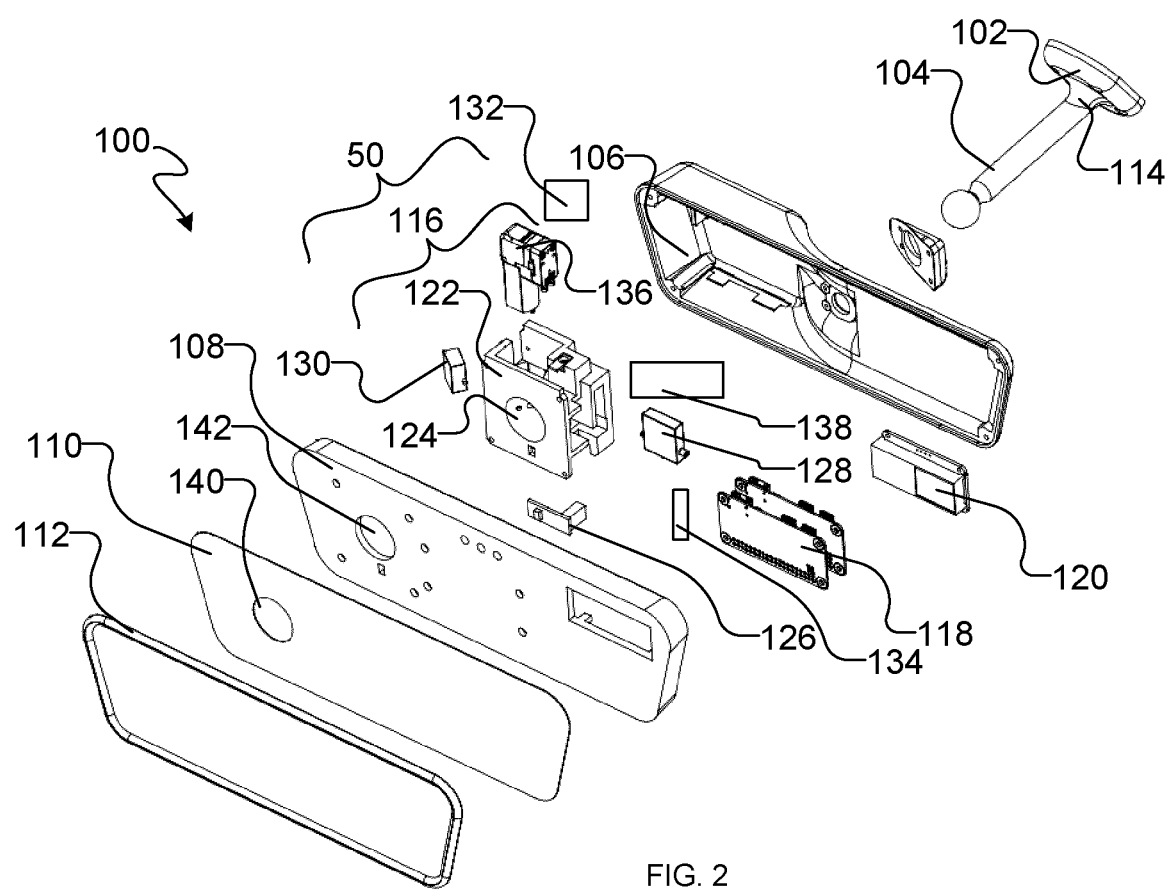
FIG. 2 shows an exploded view of the contact-free breath analysis apparatus depicted in FIG. 1.

As shown in more detail in FIG. 2, rearview mirror 100 has a mirror glass 110 that provides the reflective surface of the mirror. A mirror bezel 112 secures mirror glass 110 in place against front housing 108. A mirror clamp 114 is provided to secure base 102 to connector arm 104.

A sensor module 116 is provided within rearview mirror 100 as part of contact-free breath analysis apparatus 50 to facilitate the detection of substances from a breath sample from a subject as described below. Apparatus 50 also includes one or more appropriate printed circuit boards 118 or other suitable controller to facilitate the operation thereof, as well as an LED display module 120. While the output display has been illustrated as an OLED screen in the exemplary embodiment illustrated, in other embodiments any other type of display screen could be used, including an LCD display screen.

In more detail with reference to FIG. 2, sensor module 116 includes a sensor housing 122. Sensor housing 122 defines an inlet cone 124 that funnels an incoming breath sample to the various sensors of sensor module 116. While illustrated as having a generally conical shape, in other embodiments, inlet cone 124 could be provided with other shapes, such as circular, trapezoidal, oval, rectangular, or as a small aperture.

In various embodiments, different sensors can be deployed in sensor module 116 depending on the target analyte of interest. Also, while the various sensors used have been illustrated as being deployed within sensor module 116, in other embodiments the various sensors used can be dispersed at any desired location within apparatus 50. For example, temperature and/or humidity sensor 134 can be deployed adjacent to inlet cone 124 rather than being provided within inlet cone 124.

In some embodiments, including the illustrated embodiment, one of the sensors provided in sensor module 116 is a proximity sensor 126. Proximity sensor 126 functions to determine the distance between a user and sensor module 116, for example as illustrated as 512 in FIG. 3. Proximity sensor 126 can be used to ensure that a subject is appropriately positioned to provide a functional breath sample to apparatus 50. In some embodiments, two proximity sensors 126 could be provided at a known spaced-apart interval (for example half the face width of an average person's head), to determine if the user's head is properly centred around inlet cone 124. In alternative embodiments, a camera could be used to do one or more of: measure a distance from a user to mirror glass 110, determine if a user's head is properly centred around inlet cone 124, and/or uniquely identify the user or preserve a record of the user's image for subsequent verification. The camera could be a camera for capturing static images, e.g. photographs, and/or for capturing moving images, e.g. video. In some embodiments, the camera is used to perform facial recognition to confirm the identity of the user of apparatus 50.

Sensor module 116 also includes an analyte sensor 128 to detect the target substance of interest in the subject's breath. In the illustrated embodiment, sensor 128 is a quad cell fuel cell sensor that is used to detect alcohol in the subject's breath sample. In alternative embodiments, suitable sensors for detecting other substances in the subject's breath sample (e.g. cannabis) could additionally or alternatively be provided.

In some embodiments, including the illustrated embodiment, a pressure sensor 130 is provided. Pressure sensor 130 assists in determining that a subject has exhaled breath with a sufficient pressure, within a target pressure range, and/or with an acceptable pressure profile so that a satisfactory breath sample is provided to sensor module 116. For example, if a subject exhaled too shallowly to supply a satisfactory breath sample, then a sufficient quantity of the analyte of interest might not reach analyte sensor 128 to trigger a reading of impairment, even if the subject's blood concentration of the analyte of interest was sufficiently high as to be above an acceptable limit.

In some embodiments, including the illustrated embodiment, a carbon dioxide ($CO_2$) sensor 132 is provided. Carbon dioxide sensor 132 assists in determining when a sufficient amount of breath has been exhaled (again to help ensure that a sufficient quantity of the analyte of interest reaches analyte sensor 128 to provide an accurate reading), and can also or alternatively assist in avoiding cheating by ensuring that the airflow through sensor module 116 is actually human breath (and not, for example some type of forced air produced by a fan, air being released from a balloon, or the like). In some embodiments, an acceptable carbon dioxide response can be one or more of meeting a carbon dioxide threshold level, falling within a carbon dioxide target range, and/or falling within an acceptable carbon dioxide profile.

In some embodiments, including the illustrated embodiment, a temperature sensor and/or a humidity sensor, collectively illustrated as 134 are provided, which like carbon dioxide sensor 132 assist in determining that the airflow through sensor module 116 is actually human breath, e.g. by confirming that the temperature and/or humidity of the breath sample is one or more of: within expected ranges for human breath, above a certain limit, and/or has an acceptable profile.

In some embodiments, one or more of proximity sensor 126, pressure sensor 130, carbon dioxide sensor 132 and/or temperature and/or humidity sensor 134 can be omitted. In particular, in some embodiments if a camera is used to verify that the breath sample is being provided by a user and to assist in determining that the user's head is in an appropriate position to provide a sample, then such sensors that are used to assist in positioning the user and/or verifying that the user is providing the breath sample and not cheating in some manner are not necessary.

In some embodiments, a first pump such as a miniature diaphragm pump 136 is provided to draw the breath sample into apparatus 50. A diaphragm pump may be used in some embodiments because it is effective at the desired flow rates for breath samples, and is compatible with the relatively high humidity of exhaled breath. In some embodiments, a second pump such as a suction solenoid micro pump 138 is provided to draw one or more portions of the breath sample into the analyte sensor 128, as described in greater detail below with reference to FIG. 5. Together, miniature diaphragm pump 136 and suction solenoid micro pump 138 act to provide a convective flow of the breath sample to analyte sensor 128. While the illustrated embodiment is described with reference to miniature diaphragm pump 136 and suction solenoid micro pump 138 as examples of suitable pumps, in other embodiments any other suitable type of pump could be used, including e.g. linear pumps, Piezo pumps, piston pumps, rotary vein pumps, peristaltic pumps, or the like. In some embodiments, the first pump 136 is a constant flow pump, i.e. is able to provide a relatively constant level of fluid flow. In some embodiments, the second pump 138 is a pulsed pump, i.e. is able to be pulsed on and off to provide a pulsed fluid flow.

To enable a breath sample to reach sensor module 116, in the illustrated embodiment both mirror glass 110 and front housing 108 include apertures 140, 142 that are aligned with inlet cone 124, so that sensor module 116 can receive the breath sample provided by a subject.

In certain embodiments including the illustrated embodiment in which contact-free breath analysis apparatus 50 is provided within a mirror 100, the mirrored surface provided by mirror glass 110 can be used to provide visual feedback that can additionally assist a user with correct positioning of the user's face, mouth and lips to provide a breath sample via inlet cone 124. Specifically, because mirror glass 110 surrounds inlet cone 124, a user can visually verify via the reflection provided by mirror glass 110 that the user's lips are appropriately positioned with respect to inlet cone 124, because a user will be able to see the reflection of the location of their lips in mirror glass 110.

Further, and also applicable to embodiments in which breath analysis apparatus 50 is not provided in a mirror but is provided in a surface on which condensation of a user's breath is visible, in the case where a user is blowing the breath sample towards inlet cone 124, if the user's breath comes horizontally or vertically out of alignment with inlet cone 124 so that the flow of breath is positioned incorrectly relative to inlet cone 124, then humidity from the breath will start to condense on mirror glass 110, and the user will be provided with visible feedback indicating that the user's lips have deviated away from inlet cone 124. The user can then make corrective adjustments to the positioning of their lips to avoid and/or minimize any condensation appearing on mirror glass 110. In contrast, when the user's lips are positioned correctly horizontally and vertically relative to inlet cone 124, then the breath will be sucked into the sampling area of sensor module 116 via the action of the pumps within mirror 100. Thus, mirror glass 110 provides visual feedback to the user to ensure the correct positioning of the user's lips within a Cartesian plane parallel to the plane of the surface of mirror glass 110. The Cartesian plane parallel to the plane of the surface of mirror glass 110 is perpendicular to the fluid flow path of the breath sample provided by the user.

In alternative embodiments, instead of using a surface on which condensation of a user's breath is visible or a mirrored surface, other mechanisms could be used to provide visual feedback as to the appropriate positioning of the user's lips in the Cartesian plane perpendicular to the fluid flow path of the breath sample provided by the user. For example, appropriate proximity sensors could be used to determine the position of the user's face in such Cartesian plane perpendicular to the fluid flow path of the breath sample provided by the user, appropriate cameras could be used to determine the position of the user's face in such Cartesian plane, or so on, and feedback can be provided to the user in any suitable manner, for example by using suitable indicator lights, by audible tones, voice commands through any other means of communication that would allow a user to understand how the position of their lips should be adjusted relative to the position of inlet cone 124 in the Cartesian plane perpendicular to the fluid flow path of the user's breath sample.

In addition to regulating the horizontal and vertical positioning of a user's lips relative to inlet cone 124, proximity sensor 126 helps to regulate the spacing of the user's lips away from inlet cone 124, to ensure this spacing is within the desired range and prevent dilution or contamination of the user's breath sample with ambient air. Together these various parameters can be controlled to ensure that the cone in which the user's breath travels (illustrated as cone 514 in FIG. 3), which is reflective of the diameter of the spread of the user's breath with increasing depth from their lips, is positioned at the desired location to ensure a valid sample is provided to sensor module 116.

In some embodiments, a camera, optical scanner or other verification apparatus is provided as part of breath analysis apparatus 50, so that the identity of a user providing a specific breath sample can be verified and/or preserved for later verification.

Figure 3:
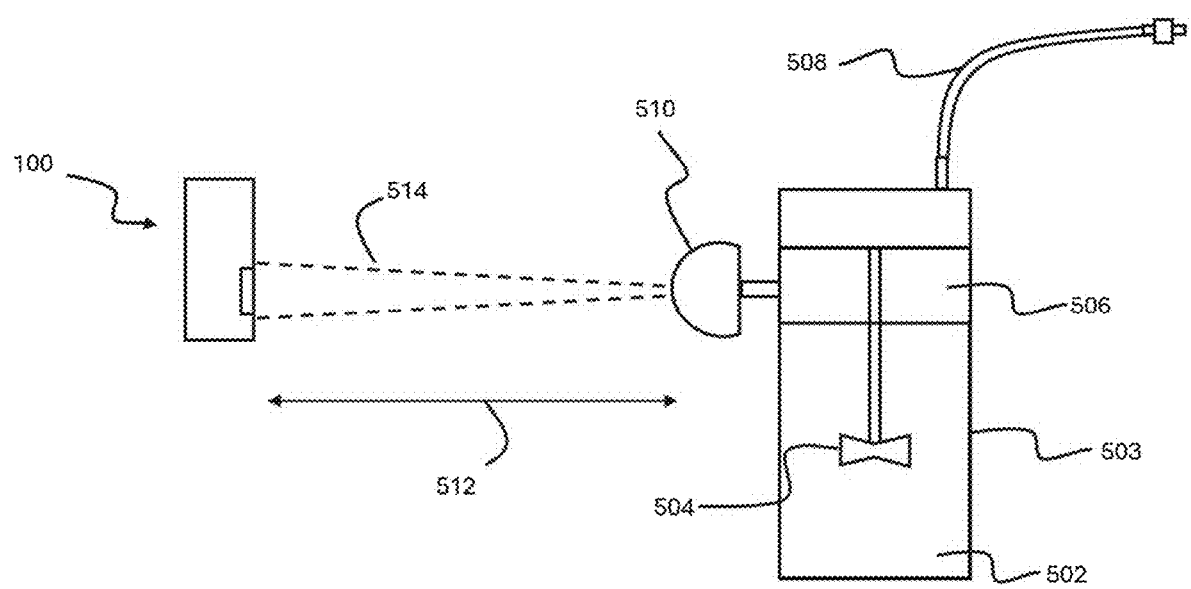
FIG. 3 shows an example embodiment of an apparatus for testing a contact-free breath analysis apparatus.

With reference to FIG. 3, an example embodiment of an apparatus for testing the contact free breath analysis apparatus 50 is illustrated. A control solution 502 containing a known amount of the target analyte (for example, a solution of alcohol corresponding to a concentration of 0.08 blood alcohol content) is provided within a container 503. Control solution 502 may include a mixing apparatus 504 to maintain an even concentration of the target analyte throughout control solution 502, and ensure that the head space 506 maintains an even concentration of the target analyte therein during any experiments. An inlet tube 508 can be provided to force air through container 503 and out of an exit, to allow for the simulation of a user blowing air towards contact free breath analysis apparatus 50. In the illustrated embodiment, the exit of container 503 is provided as a 3-D printed model of a user's lips 510, to more accurately simulate the blowing of breath by a user towards contact-free breath analysis apparatus 50. The exit in the form of user's lips 510 can be positioned a desired distance 512 from mirror glass 110. This space 512 between the user's lips and mirror 100 is what allows for the contact-free acquisition of a breath sample for analysis. For example, if distance 512 is too large, then a sufficient amount of the user's breath sample may not reach sensor module 116 to allow for accurate detection of the target substance of interest, and/or there is a greater risk of cross-contamination due to ambient air becoming entrained with the user's breath sample.

In some embodiments, including the illustrated embodiment, mirror 100 is provided with indicia for communicating various aspects of the operation of mirror 100 to a user. For example, in the illustrated embodiment, a proximity indicator light 150 is provided on the front face of mirror glass 110. Proximity indicator light 150 can be used to indicate when a user is appropriately positioned to be able to use contact-free breath analysis apparatus 50. For example, when a subject is an appropriate distance 512 away from the front face of mirror glass 110, for example between 5 cm and 10 cm, including any value therebetween, e.g. 5.5, 6.0, 6.5, 7.0, 7.5, 8.0, 8.5, 9.0 or 9.5 cm, then proximity indicator light 150 can be turned on (e.g. via printed circuit board 118), to indicate to the user that the user is appropriately positioned to be able to provide a breath sample. In other embodiments, once contact-free breath analysis apparatus 50 has been activated, proximity indicator light 150 can blink, and will continue to blink until proximity sensor 126 determines that a user is an appropriate distance 512 away from the front face of mirror glass 110. In some embodiments and by way of example only, proximity indicator light 150 is blue, to differentiate the other indicator lights provided on mirror 100.

In some embodiments, an analyte pass indicator light 152 is provided on the front face of mirror glass 110. Analyte pass indicator light 152 can be used to indicate when a user has provided a satisfactory breath sample and analyte sensor 128 has determined that the level of the target analyte (e.g. alcohol, cannabis or the like) in the user's blood is below a predetermined level (e.g. below about 0.05 BAC for alcohol). In some embodiments and by way of example only, analyte pass indicator light 152 is green.

In some embodiments, an analyte failure indicator light 154 is provided on the front face of mirror glass 110. Analyte failure indicator light 154 can be used to indicate when a user has provided a satisfactory breath sample and analyte sensor 128 has determined that the level of the target analyte (e.g. alcohol, cannabis or the like) in the user's blood is above a predetermined level (e.g. above about 0.05 BAC for alcohol). In some embodiments and by way of example only, analyte failure indicator light 154 is red.

In some embodiments, indicator lights 150, 152, 154 are LED indicator lights.

In other embodiments, rather than using indicator lights to provide feedback to a user, the information gathered from apparatus 50 can be passed to the vehicle or other piece of equipment via a communication bus such as a CAN bus, LIN, Ethernet or wireless communications protocol such as Wi-Fi, Bluetooth or the like.

In some embodiments, additional indicator lights or indications or other feedback, e.g. audible feedback, could be provided. For example, if a subject provides a breath sample and sensor module 116 determines that the breath sample is not acceptable (for example because a threshold level of one or more of pressure, humidity, carbon dioxide, or volume or the like is determined to not be met), then a yellow light could be activated and/or analyte failure indicator light 154 could blink, to indicate that the sample was not acceptable and that a further sample should be provided. In other embodiments, if the breath sample is not acceptable, appropriate prompts could be displayed to the user via LED display module 120, e.g. "BLOW HARDER" or the like, to indicate what the user needs to do to provide an acceptable breath sample. In other embodiments, an alarm buzzer can sound to indicate that an acceptable breath sample was not provided, or the like. An assessment of the target analyte will not be provided if an acceptable breath sample has not been provided.

In some embodiments, in addition to or as an alternative to analyte pass/failure indicator lights 152, 154, LED display module 120 provides a visual output 156 on mirror glass 110 confirming the measured level of analyte detected by analyte sensor 128, e.g. 0.08 BAC in the illustrated embodiment of FIG. 1. In some embodiments, LED display module 120 can provide additional indicia, such as displaying the wording PASS, FAIL, or PROVIDE NEW SAMPLE, to indicate that the level of analyte present is acceptable or unacceptable, or that the breath sample provided was unacceptable.

In some embodiments, sensor module 116 provides a response time of less than 10 seconds after an acceptable breath sample has been provided. In some embodiments, sensor module 116 has a recovery time of 30 seconds before a new breath sample can be provided for assessment.

Figure 4:
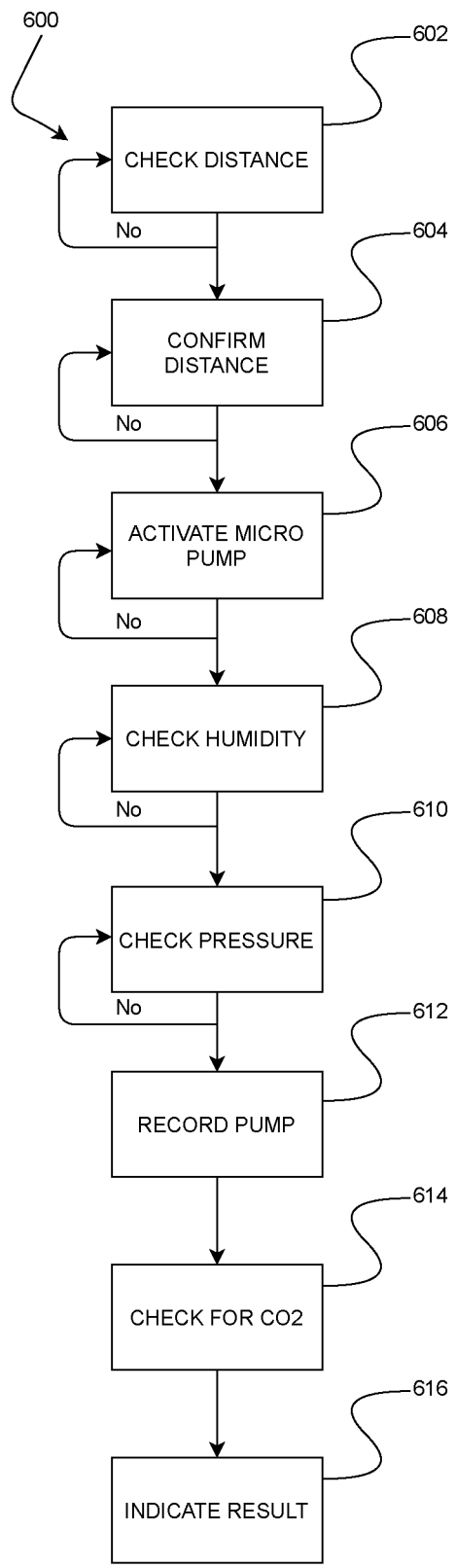
FIG. 4 shows an example method of obtaining and analyzing a breath sample using a contact-free breath analysis apparatus.

With reference to FIG. 4, an example embodiment of a method 600 for carrying out a contact-free breath analysis is illustrated. In some embodiments, method 600 can be carried out using mirror 100, although other apparatus can also be used to carry out method 600 in alternative embodiments.

At step 602, the distance 512 between the user and the contact-free breath analysis apparatus 50 is determined, e.g. using proximity sensor 126. If proximity sensor 126 determines that the distance between the user and the contact-free breath analysis apparatus 50 is too high or too low, apparatus 50 may supply indicia to the user indicating that the distance 512 is not yet appropriate for providing a sample. For example, in some embodiments, proximity indicator light 150 may flash if distance 512 is too large or too small. In other embodiments, LED display module 120 could be used to supply other indicia, e.g. CLOSER if distance 512 is too large or FARTHER if distance 512 is too small. In still other embodiments, an audio module could be integrated into apparatus 50 and verbal feedback or a tone could be provided to tell the user to move closer to or farther away from apparatus 50.

At step 604, once proximity sensor 126 determines that distance 512 is the desired distance, an indication to this effect is provided to the user. For example, proximity indicator light 150 may remain solidly illuminated if distance 512 is appropriate for providing a contact-free breath sample. In alternative embodiments, LED display module 120 could be used to confirm that distance 512 is appropriate, for example by displaying indicia such as BLOW or PROCEED, so that a user knows that the provision of the breath sample can be initiated. In still other embodiments, an audio module could be used to provide such indications to a user, either verbally or via suitable tones or beeps or the like.

At step 606, after the proximity condition has been met at 604, miniature diaphragm pump 136 is actuated to pull the provided breath sample into contact-free breath analysis apparatus 50, and suction solenoid micro pump 138 can be activated, optionally in pulses, to draw a portion of the provided breath sample towards analyte sensor 128 so that measurements of any target analyte present in the breath sample can be obtained. In some embodiments, miniature diaphragm pump 136 is operated as a constant flow pump. In some embodiments, suction solenoid micro pump 138 is operated as a pulsed pump.

By operation of pumps 136, 138 (and any reference to pumps 136, 138 includes a corresponding reference to pumps 736, 738 and any other first and second pumps described herein) the breath sample can be supplied to analyte sensor 128 via convective flow (i.e. by an active fluid flow rather than by passive diffusion). In alternative embodiments, the breath sample can be supplied to analyte sensor 128 by diffusion based flow instead of by convective flow. In such embodiments, suction solenoid micro pump 138 can be used to purge separation channel 744 in embodiments in which separation channel 744 is provided.

Without being bound by theory, it is believed the first pump 136 assists in obtaining the breath sample in a contact-free manner with a controlled flow rate for delivery to main fluid flow path 746. The second pump 138 assists in ensuring a sufficient amount of this controlled flow of breath sample is delivered from the main fluid flow path 746 to the analyte sensor 128.

In some embodiments, after the proximity condition has been met at 604, an indication such as an audible tone or a suitable indicator light is given to the user to indicate that the user should start blowing to provide the breath sample. In some embodiments, after a user has started to provide a breath sample, additional proximity sensors and/or a camera can be used to verify that the position of the user's lips in a Cartesian plane perpendicular to the fluid flow path of the user's breath sample is appropriate relative to inlet cone 124 and provide appropriate feedback if not, and/or the user can receive visual feedback from mirror glass 110 to verify the proper positioning of their lips in said Cartesian plane, and/or the user can receive visual feedback from the formation of condensation around inlet cone 124 on mirror glass 110 (or on the surface on which condensation is visible in other embodiments that do not use mirror glass 110 but instead provide a surface on which condensation is visible around inlet cone 124). Based on such feedback, the user can adjust the position of their lips in the Cartesian plane perpendicular to the fluid flow path of the user's breath sample.

At step 608, humidity sensor 134 is used to evaluate the relative humidity of the breath sample. If the humidity level is outside a desired range, for example too low or too high, appropriate feedback can be given to the user, for example via appropriate indicator lights to indicate that the breath sample being provided is not acceptable and that a new sample needs to be provided. For example, if a user is attempting to cheat by using a fan, expelling air from a balloon or the like, the humidity will be too low and apparatus 50 will not accept the breath sample as sufficient for providing a pass or failure determination.

In some embodiments, at step 608, the temperature of the breath sample is evaluated. In some embodiments, the temperature and humidity sensors are both provided as part of a single module provided as 134, and so at step 608 a determination of both humidity and temperature is made. A temperature reading can likewise be used to verify that the sample provided is human breath by ensuring that the temperature of the breath sample is within a range of expected temperatures for human breath.

At step 610, pressure sensor 130 is used to evaluate the pressure of the provided breath sample. If the pressure is outside a desired range, for example too low or too high, appropriate feedback can be given to the user, for example via appropriate indicator lights, LED display module 120 and/or audible indicia, to indicate that the breath sample being provided is not acceptable and that a new sample needs to be provided. For example, if the subject blows with too low a pressure, the provided breath sample may not contain air from within the subject's lungs, and may be less likely to provide an accurate determination of the user's actual blood concentration of the target analyte of interest. Also as an example, if the user is not blowing towards inlet cone 124, the pressure measured by pressure sensor 130 may indicate that the breath sample is not being provided in the desired manner.

At step 612, after it has been determined that the humidity and pressure of the provided breath sample are within predetermined acceptable levels, suction solenoid pump 138 can be activated, optionally in a pulsed manner, to start directing sample through any separation channel such as separation channel 744 and to analyte sensor 128, and recording of sensor data is commenced. In some embodiments, suction solenoid pump 138 is pulsed e.g. 12 times to pull the breath sample to analyte sensor 128 for detection of the target analyte. For example, in embodiments in which analyte sensor 128 is a fuel cell sensor for detecting alcohol, as the breath sample is pulsed through the analyte sensor 128 by suction solenoid micro pump 138, the output voltage of the fuel cell gradually increases in proportion to the blood alcohol content, and the amplitude of the output voltage signal (from maximum to minimum) with such pulsing can be used to calculate the blood alcohol content.

At step 614, after recording has proceeded for a suitable period of time, e.g. 30 seconds, the concentration of carbon dioxide measured by carbon dioxide sensor 132 is checked. Checking the level of carbon dioxide can help to prevent cheating, since the expected concentration of carbon dioxide in human breath is known, whereas a "sample" provided by a cheating user attempting to use a fan or expel air from a balloon or the like will not include a sufficiently high concentration of carbon dioxide. In some embodiments, the carbon dioxide sensor used as 132 may work on photo or acoustic sensing principles, and may not be able to make a rapid determination of carbon dioxide levels (e.g. taking as long as 2-5 seconds to provide a response). Thus, the initial detection of analyte by analyte sensor 128 is permitted to proceed, and subsequently the level of carbon dioxide measured in the background by carbon dioxide sensor 132 is checked. In some embodiments, once the level of carbon dioxide has been determined, the breath test can be interrupted if the level of carbon dioxide was not determined to be within desired parameters, or the breath test can be permitted to complete and the result displayed to the user if the level of carbon dioxide was determined to be within the desired parameters.

Checking some or all of the humidity, temperature and carbon dioxide content of the provided breath sample can help to provide multiple checks to ensure that the sample provided is human breath, and not a user attempting to cheat by supplying some other source of forced air to apparatus 50.

At step 616, the result of the contact-free breath analysis is supplied to a user in any desired manner. For example, if it is determined that the user has provided an acceptable breath sample and that the concentration of the target analyte in the user's blood is within an acceptable limit, green indicator light 152 may be illuminated, LED display module 120 may display an indication such as PASS, audible feedback such as a tone or verbal confirmation may be provided, or so on.

If it is determined that the user has provided an acceptable breath sample and the concentration of the target analyte in the user's blood is above an acceptable limit, red indicator light 154 may be illuminated, LED display module 120 may display an indication such as FAIL, audible feedback such as a tone or verbal statement may be provided, or so on.

If it is determined the user has not provided an acceptable breath sample, then an appropriate indication may be outputted to indicate to the user that a fresh breath sample needs to be provided, for example red indicator light 154 may blink or a separate yellow indicator light may be illuminated, LED display module 120 may display an indication such as NEW SAMPLE, audible feedback such as a tone or verbal request may be provided, or so on.

In some embodiments, LED display module 120 displays a quantitative reading such as visual output 156, to indicate the measured level of the target analyte of interest in the user's blood.

Figure 5:
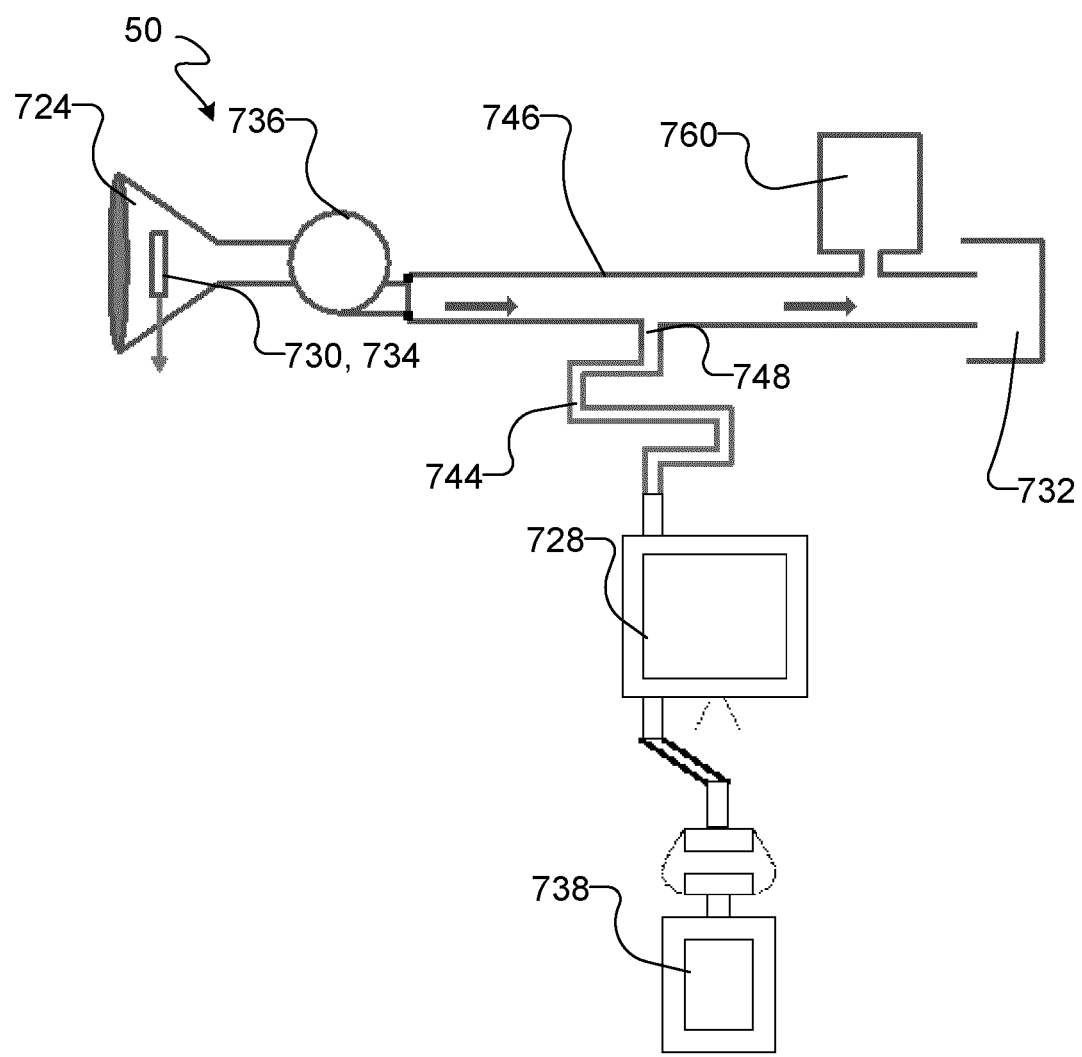
FIG. 5 shows an example embodiment of a contact-free breath analysis apparatus.

As shown in greater detail in FIG. 5 in which reference numerals incremented by 600 have been used to refer to corresponding elements of contact-free breath analysis apparatus 50, in one example pneumatic circuit used in some embodiments, a second pump such as a miniature diaphragm pump 736 is provided to draw a breath sample into a main fluid flow path 746 of apparatus 50. In some embodiments, a first pump that is a suction solenoid micro pump 738 is provided to draw the breath sample into analyte sensor 728 via sample fluid flow path 748. Analyte sensor 728 can be provided downstream of a separation channel such as a selectivity channel or a microfluidic channel, illustrated as 744, to allow for separation of substances in the separation channel before detection by analyte sensor 728, which can increase sensitivity and/or allow the differentiation of background substances (e.g. hand sanitizer) that are not contained in the breath sample as expelled by the user but which have become entrained in the breath sample prior to entry into apparatus 50.

In some embodiments, including the illustrated embodiment, a pressurized chamber 760 is provided at a downstream end of main fluid flow path 746. The combined action of miniature diaphragm pump 736 and pressurized chamber 760 generates a positive pressure inside of main fluidic path 746, i.e. the pressure inside of main fluidic path 746 is higher than atmospheric pressure. This positive pressure in combination with the suction generated by suction solenoid micro pump 738 causes the air flow along sample fluid flow path 748 (and therefore the flow through separation channel 744) to be dependent on (and controllable by) the magnitude of the pressure established by miniature diaphragm pump 736 and suction solenoid micro pump 738 and the dimensions of separation channel 744. The flow mechanism of substances including the target analyte through separation channel 744 is also dependent on the magnitude of such established pressure. In some example embodiments, the estimated airflow within main fluid flow path 746 is in the range of about 300 to about 400 mL/minute, including any value therebetween e.g. 310, 320, 330, 340, 350, 360, 370, 380 or 390 mL/minute. Thus, apparatus 50 is able to supply the breath sample to sample fluid flow path 748 (and therefore separation channel 744 and analyte sensor 728) via convective fluid flow rather than by passive diffusion.

In some embodiments, without being bound by theory, the use of convective fluid flow to deliver the breath sample to analyte sensor 728 allows for rapid response but still allows for a good degree of selectivity, and separation channel 744, which can be any type of selectivity or separation channel including a microfluidic channel can be used to enhance selectivity. This allows analyte sensor 728 to identify the unique fingerprint of a target analyte in the sample, which can be identified using machine learning and/or mathematical processing.

In alternative embodiments, pressurized chamber 760 can be used to collect a sample containing the breath for analysis by other sensors (e.g. other VOC sensors) for further analysis. For example, such sample may be used to detect the presence of tetrahydrocannabinol or other controlled substances in the bloodstream of a user. In other embodiments, analyte sensor 728 can be used to detect any desired analyte, for example tetrahydrocannabinol or other controlled substances, disease biomarkers, dust, environmental pollutants, or so on.

Generally speaking, microfluidic gas detectors use a passive diffusion approach, wherein the migration of gas molecules along the channel is limited by the diffusion rate and physical adsorption/desorption rates of the molecules to the channel walls. Without being bound by theory, diffusion as a passive method of detection, as is typically used in microfluidic devices, is time intensive, and cannot be used to provide a rapid determination. Thus, passive diffusion may be undesirable if it is desired to rapidly provide an indication of impairment to a user. In contrast, the controlled convective flow mechanism provided by miniature diaphragm pump 736 and suction solenoid micro pump 738 provides a balance between selectivity and time-efficiency which can be desirable in some embodiments.

Figure 6:
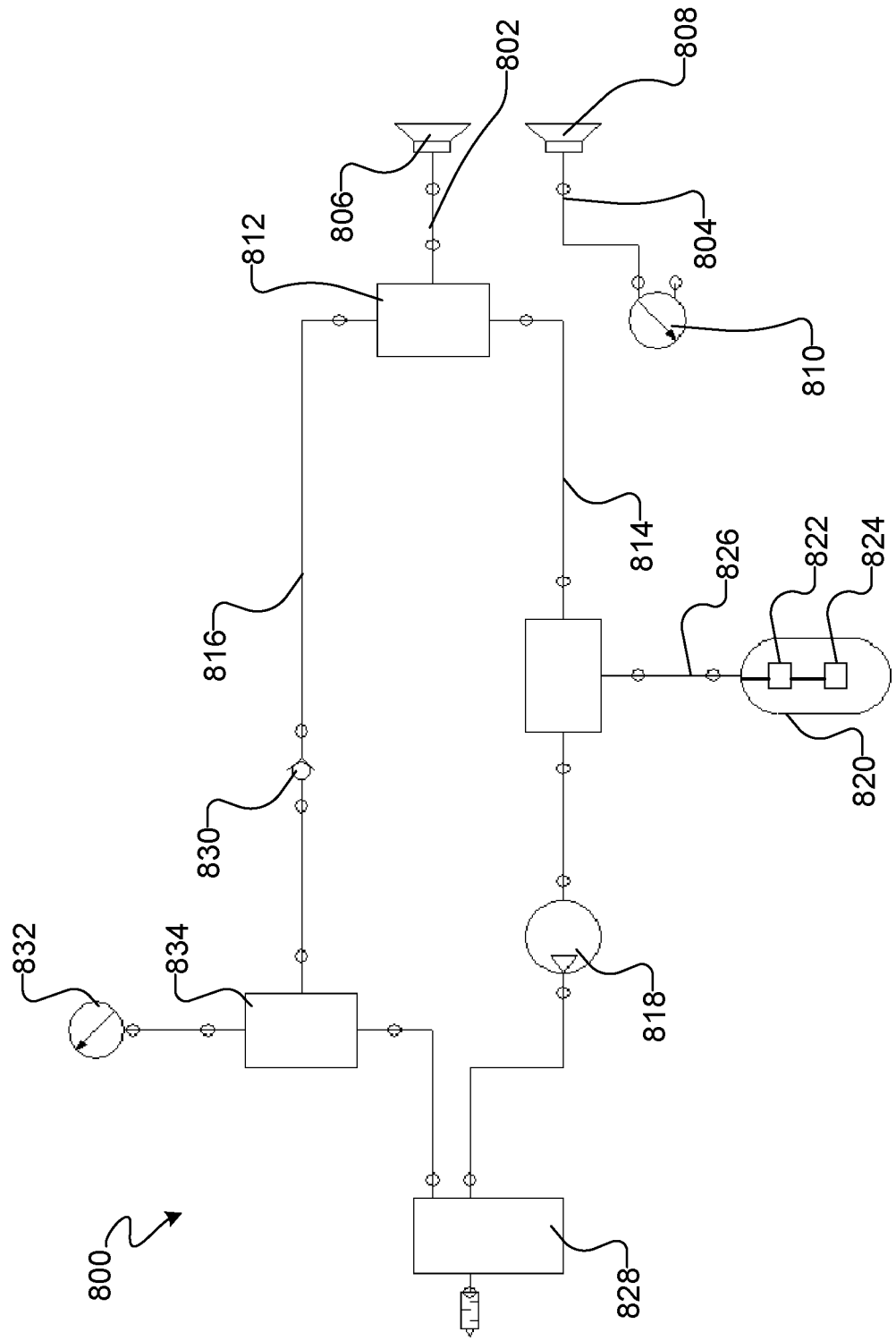
FIG. 6 shows a pneumatic circuit for an exemplary apparatus of a contact-free breath analysis apparatus that can be used either in a contact-free manner, or in conjunction with a mouthpiece to contain the input breath sample.

With reference to FIG. 6, a second example of an exemplary pneumatic circuit 800 that can be used for a contact-free breath analysis apparatus that can be used either in a contact-free manner, or in conjunction with a mouthpiece to contain the input breath sample, is illustrated. Pneumatic circuit 800 has two distinct fluid flow paths 802 and 804 for receiving a breath sample from a user. A first inlet nozzle 806 is positioned to deliver a breath sample to first fluid flow path 802, and a second inlet nozzle 808 is positioned to deliver a breath sample to a second fluid flow path 804. First and second fluid flow paths 802 and 804 are fully separated, i.e. not connected, i.e. fluid does not flow between fluid flow paths 802 and 804.

When the breath analysis apparatus is being used in a contact-free manner, the user's breath is directed towards both first and second inlet nozzles 806, 808. When the breath analysis apparatus is being used with a straw, tube or other mouthpiece, the mouthpiece is fluidly coupled to first inlet nozzle 806, so that the user's breath is only received by first inlet nozzle 806.

When the breath analysis apparatus is being used in a contact-free manner, second inlet nozzle 808 directs a portion of the user's breath through second fluid flow path 804, to a pressure sensor 810. In some embodiments, pressure sensor 810 is a differential pressure sensor. Any suitable type of pressure sensor can be used, for example absolute pressure sensors, gauge pressure sensors, differential pressure sensors, vacuum (Pirani) pressure sensors, sealed pressure sensors, piezoelectric pressure sensors, or the like. When pressure sensor 810 detects pressure from a breath sample provided by a user, pressure sensor 810 activates components on first fluid flow path 802 of pneumatic circuit 800 to analyze the breath sample.

The portion of the breath sample provided through first fluid flow path 802 meets a T-junction 812 that allows fluid flow between a sampling arm 814 of first fluid flow path 802 and a regulating arm 816 of first fluid flow path 802. When pressure sensor 810 detects that a breath sample is being provided in a contact-free manner, this means that the breath sample will be entering first inlet nozzle 806 at or slightly above atmospheric pressure. Accordingly, a diaphragm pump 818 positioned on sampling arm 814 is actuated to draw the breath sample into the sampling arm 814. Diaphragm pump 818 can be positioned upstream or downstream of the sensor cartridge 820 on sampling arm 814; in the illustrated embodiment, diaphragm pump 818 is positioned downstream of sensor cartridge 820.

Sensor cartridge 820 contains an analyte sensor 822 for detecting the target analyte of interest, and a suction pump 824 for drawing a portion of the breath sample out of sampling arm 814 and through analyte sensor 822. In the illustrated embodiment, sensor cartridge 820 is in fluid communication with sampling arm 814 through a passageway 826. In some embodiments, passageway 826 can comprise a selectivity channel, a separation channel, a microfluidic channel, or the like, which can help to enhance the selectivity of analyte sensor 822 (for example, to differentiate perfumes or hand sanitizers from alcohol in the bloodstream of a user). In other embodiments, passageway 826 simply provides a fluid passageway and has no specific or special properties. In the illustrated embodiment, suction pump 824 has been illustrated as being positioned downstream of analyte sensor 822, but in alternative embodiments, suction pump 824 could be positioned upstream of analyte sensor 822.

Suction pump 824 serves to draw a desired amount of the breath sample from sampling arm 814 into analyte sensor 822 to enable a valid assessment of the presence or absence of the target analyte of interest in the user's bloodstream. For example, in some embodiments, suction pump 824 draws a volume of approximately 0.35 to approximately 0.5 mL through the analyte sensor 822.

Excess breath sample passing through sampling arm 814 is forced to exhaust 828 and out of sampling arm 814 as the user continues to provide the breath sample. After the breath sample has been provided and the breath test is complete, diaphragm pump 818 is operated for a period of time, e.g. between about 20 to 40 seconds, to purge the system and ensure analyte sensor 822 is not impacted by any residual contamination from the breath test when the next breath test is performed. A longer purge period may be used in instances where the breath test was positive for the subject analyte than in instances where the breath test was negative for the subject analyte.

If a user couples a mouthpiece such as a straw or tube to inlet nozzle 806, the breath sample provided by the user will flow exclusively through that mouthpiece and fluid flow path 802, and pressure sensor 810 will not be activated. In such cases, diaphragm pump 818 is not activated, and the user's breath sample is pressurized because it is forced through the mouthpiece. In this mode of operation, the user's breath will split at T-junction 812, with a first portion of the breath sample flowing through sampling arm 814 and a second portion of the breath sample flowing through regulating arm 816.

When used with a mouthpiece, the portion of the user's breath flowing through sampling arm 814 is pressurized, and suction pump 824 can be used to draw a sufficient amount of the breath sample through analyte sensor 822 to enable a valid assessment of the presence or absence of the target analyte of interest in the user's bloodstream. Subsequent to the provision of the breath sample, diaphragm pump 818 can be activated to purge analyte sensor 822.

The portion of the user's breath sample flowing through regulating arm 816 will be allowed to flow through one-way valve 830, which in the illustrated embodiment is a check valve and through which the user's breath sample can flow by meeting the cracking pressure of that check valve, which allows air to flow only downstream in regulating arm 816. In this way, when diaphragm pump 818 is activated during the provision of a breath sample in a contact-free manner, external air cannot be drawn through regulating arm 816 and into sampling arm 814.

From one-way valve 830, the user's breath sample flows to a second T-junction 834, where the breath sample splits to exhaust 828 and a second pressure sensor 832. In embodiments in which the breath sample is provided through a mouthpiece, pressure sensor 810 is not exposed to the breath sample and so pressure sensor 832 is used to calculate the flow rate and volume of the provided breath sample to assist in verifying that an acceptable breath sample has been provided. Further, pressure sensor 832 is provided on regulating arm 816 rather than on sampling arm 814 to avoid any impact on the measurements taken by pressure sensor 832 due to the action of pump 818. In alternative embodiments, a flow meter or other suitable device could be used to evaluate the flow rate and volume of the provided breath sensor.

In some embodiments, a method of using pneumatic circuit 800 to analyze a breath sample is provided. In some embodiments, when a breath sample is provided in a contact-free manner, the user's breath flows through both of inlets 806 and 808 into fluid flow paths 802 and 804. In such embodiments, when pressure sensor 810 detects that a breath sample is being provided through second inlet 808, pump 818 is actuated to draw the user's breath sample through sampling arm 814. One-way valve 830 prevents the suction generated by pump 818 from drawing air through regulating arm 816 and intermingling such air with the provided breath sample. Thus, the user's breath sample flows through sampling arm 814, and pump 824 can be used to draw a portion of the provided breath sample to analyte sensor 822 for analysis.

In some embodiments of using pneumatic circuit 800 to analyze a breath sample, the user provides the breath sample through a sampling tube, for example a straw. The sampling tube is fluidly coupled to inlet 806 and the user blows. Because the breath sample is being provided directly through inlet 806, no portion of the user's breath flows through inlet 808 or second fluid flow path 804, and so pressure sensor 810 does not detect any pressure. In such embodiments, the user's breath can be used to activate pump 818 if desired, or pump 818 could be left turned off and only the pressure of the user's breath sample could be used to move the breath sample through sampling arm 814. Pump 824 can be activated to draw a portion of the provided breath sample to analyte sensor 824 for analysis. Also, the pressure of the user's breath sample will exceed the cracking value of one-way valve 830, allowing the valve to open so that the user's breath sample can flow to pressure sensor 832. Pressure sensor 832 (or any other suitable device used in its place) can then be used to determine the volume of the sample provided by the user. The user's breath sample can flow from both sampling arm 814 and regulating arm 816 through exhaust 828 to exit the system.

Pneumatic circuit 800 can be used as described above to analyze a plurality of different breath samples provided in either a contact-free manner or by using a sample tube. In either case, i.e. a contact-free or sample tube method of operation, pump 818 can be actuated for a period of time, e.g. between 20 and 40 seconds, after the user has provided the breath sample to purge the system and ensure analyte sensor 822 is able to accurately evaluate the status of the next breath sample to be provided without contamination.

Either of the pneumatic circuits illustrated in FIGS. 5 and 6 can be used in conjunction with any of the embodiments described and illustrated herein, for example disposed in a rearview mirror as for apparatus 50, in a steering wheel as for apparatus 900, or in a cabinet-mounted unit as for apparatus 1000 or 1400.

Figure 7A:
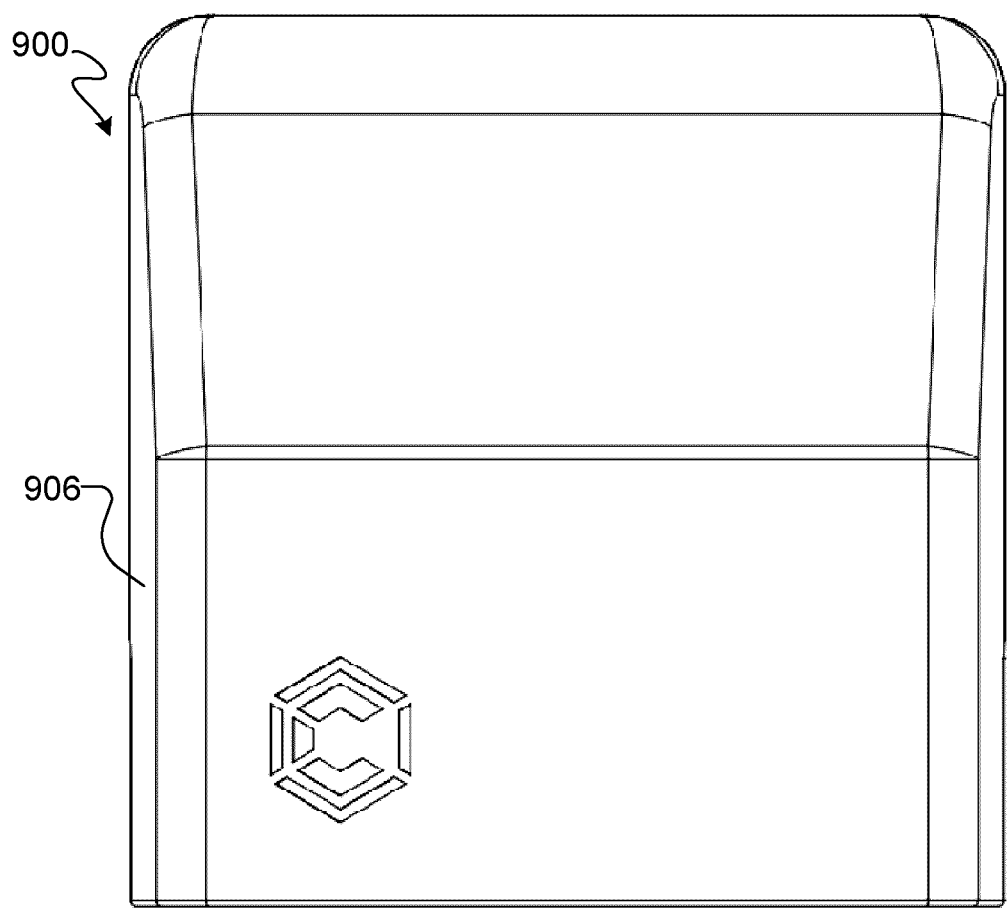
FIG. 7A shows an example embodiment of a contact-free breath analysis apparatus that can be mounted in a steering wheel.
Figure 7B:
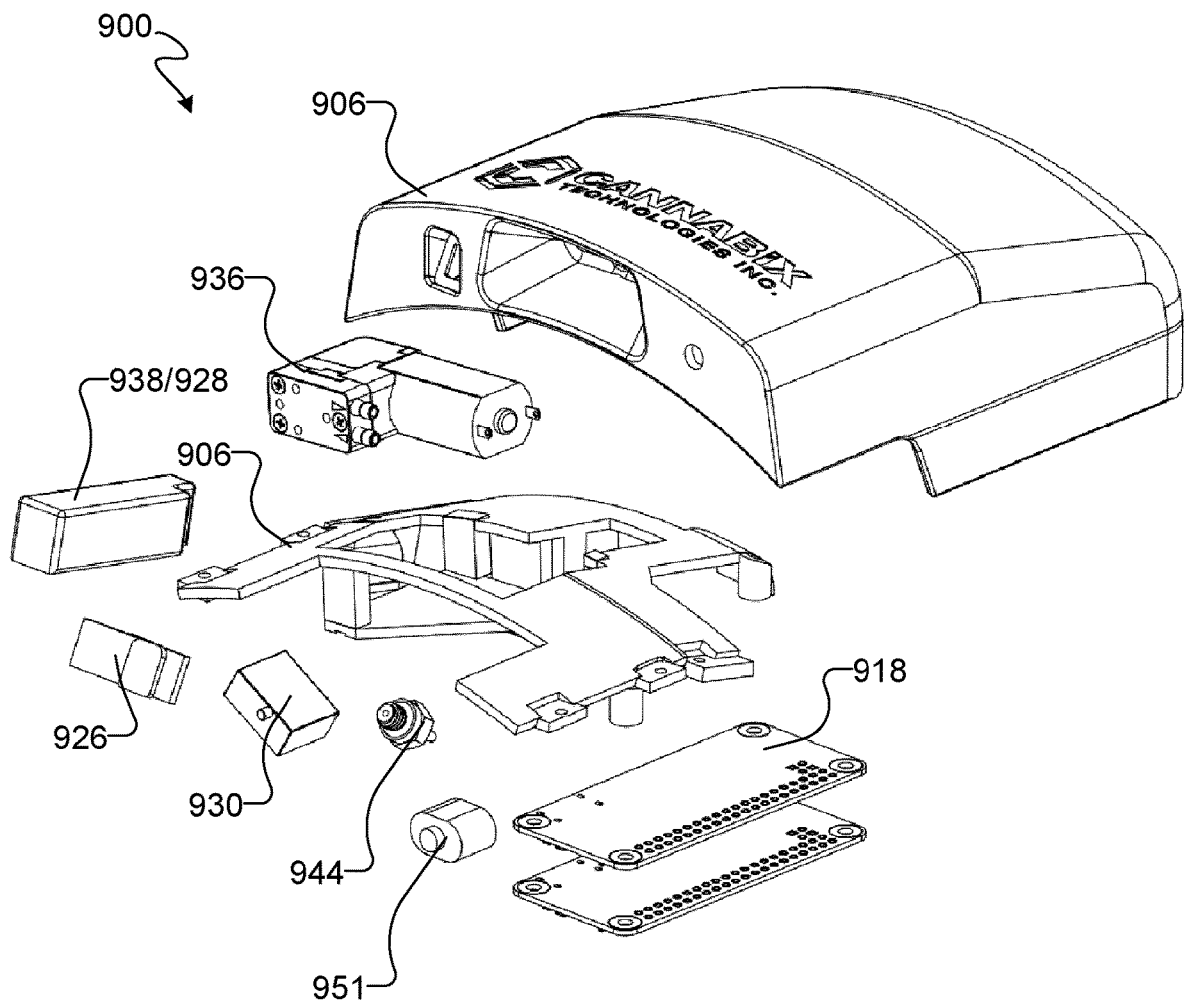
FIG. 7B shows an exploded view thereof.
Figure 7C:
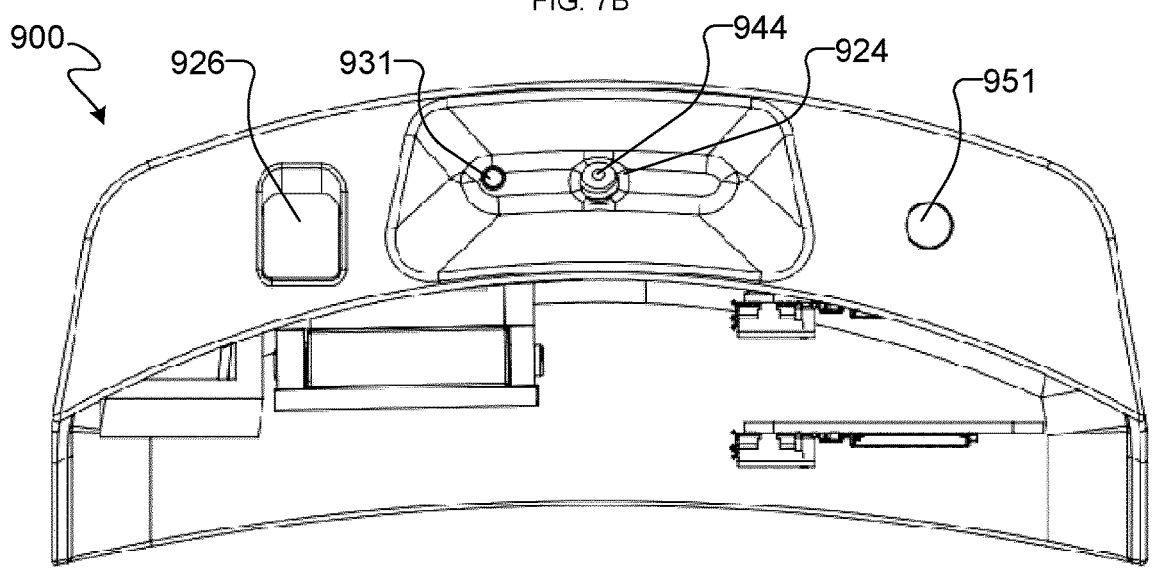
FIG. 7C shows a front view thereof.

With reference to FIGS. 7A, 7B and 7C, an example embodiment of a contact-free breath analysis apparatus 900 that can be mounted in a steering wheel is illustrated. Apparatus 900 includes generally similar features to apparatus 100, and various embodiments of apparatus 900 can include any of the features previously described for apparatus 100, with the configuration modified to fit into a steering wheel rather than into a rearview mirror. Apparatus 900 has an exterior housing 906 that covers the components of the breath collection and sensing apparatus. A diaphragm pump 936 is provided to help draw the breath sample into apparatus 900. A combination sampling pump 938 and analyte sensor 928 is provided, as is a proximity sensor 926. A holding panel housing 906 is also provided to secure the components of apparatus 900 in position. A pressure sensor 930 is provided to help evaluate the pressure of the supplied breath sample and prevent cheating as described above, with a pressure sensor inlet 931 provided so that a contact-free breath sample can reach pressure sensor 930. An inlet cone 924 is provided to funnel an incoming breath sample into the various sensors of breath analysis apparatus 900, and in some embodiments including the illustrated embodiment a nipple connector 944 is provided at the base of inlet cone 924 to allow supply of the breath sample to the pneumatic circuit included in apparatus 900. An LED holder 951 is provided to facilitate using an LED to communicate output from apparatus 900, for example as described above, and a printed circuit board 918 is provided to control the operation of apparatus 900.

With reference to FIGS. 8A-8F, an example embodiment of a contact-free breath analysis apparatus 1000 that is mounted within a standalone cabinet is illustrated. In this embodiment, the sensor unit is modular and can be easily removed and replaced, for example to avoid a need to periodically recalibrate the sensor within apparatus 1000, the entire sensor unit can simply be periodically removed and replaced.

Figure 8A:
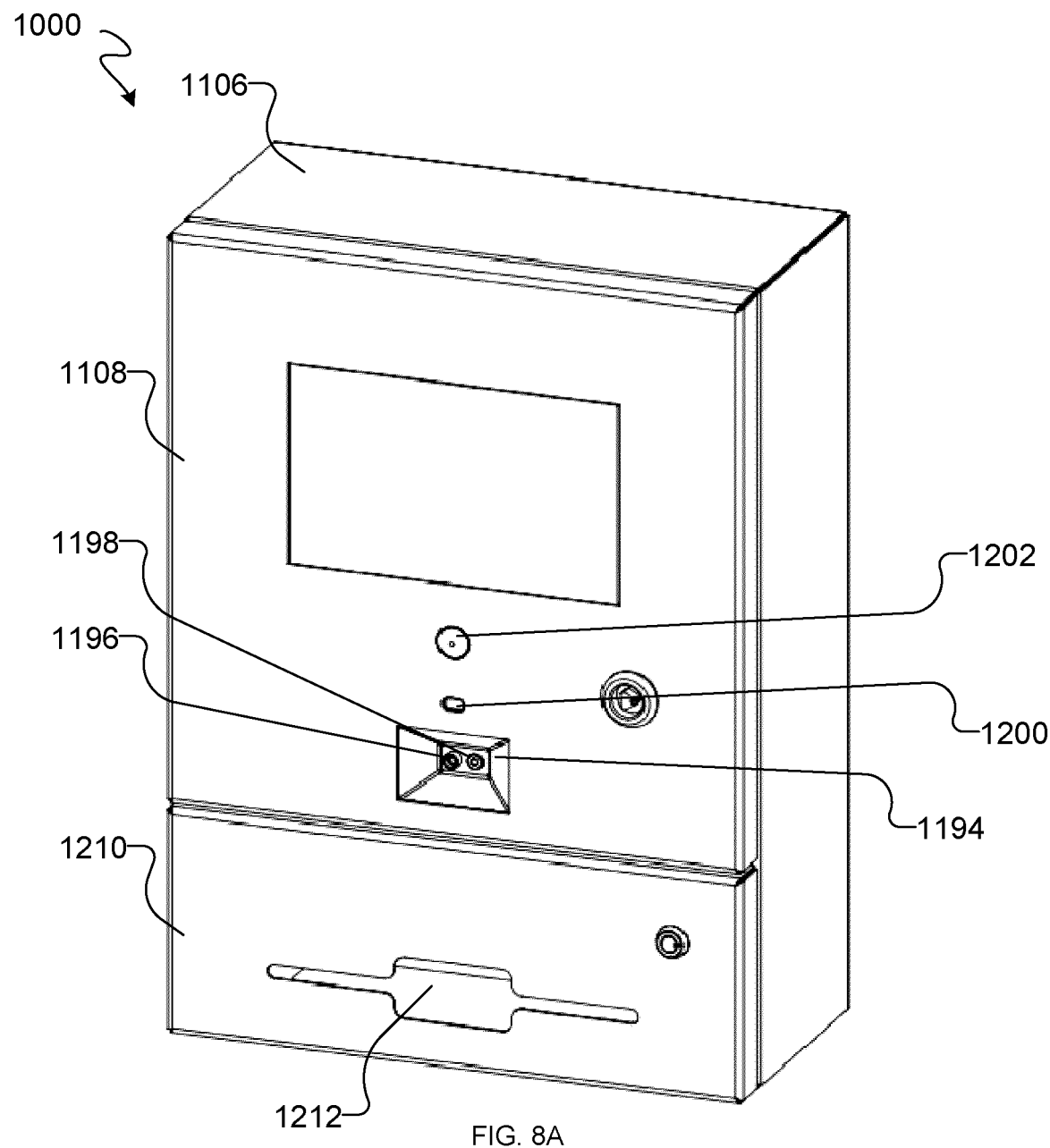
FIG. 8A shows an example embodiment of a contact-free breath analysis apparatus that is mounted within a stand-alone cabinet.
Figure 8B:
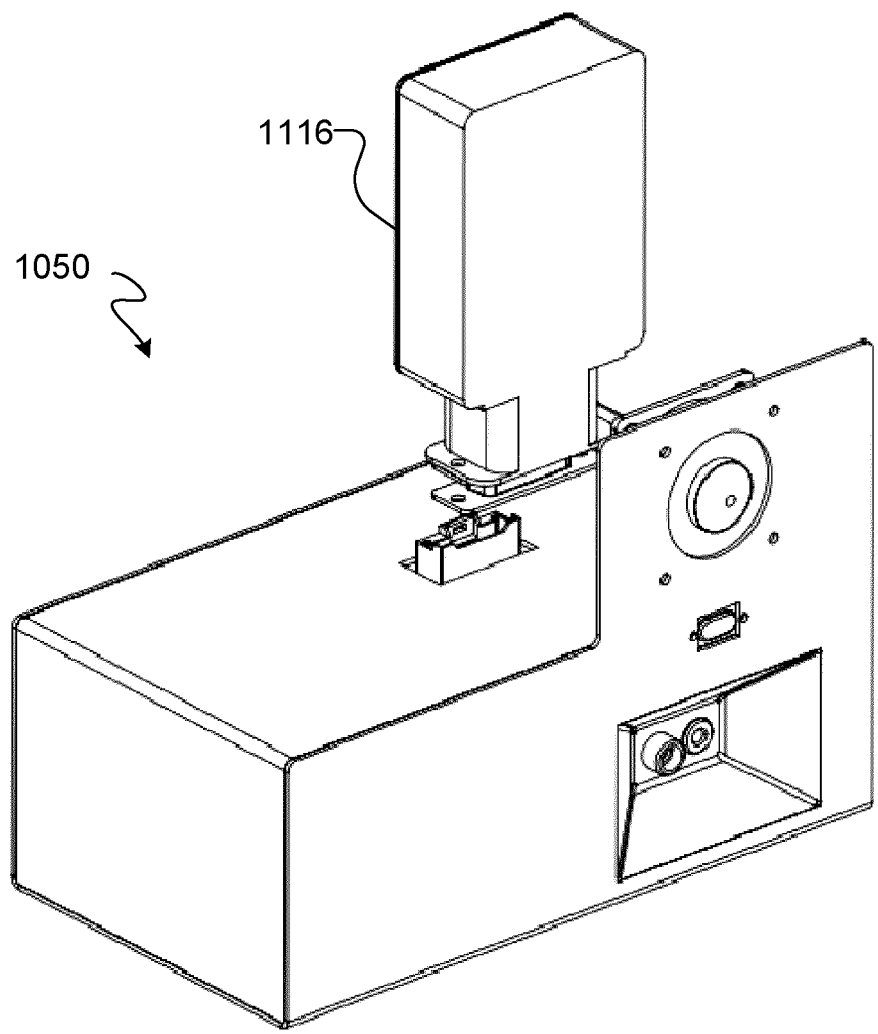
FIG. 8B shows the lower portion thereof, illustrating how a replaceable sensor cartridge can be inserted thereon.
Figure 8C:
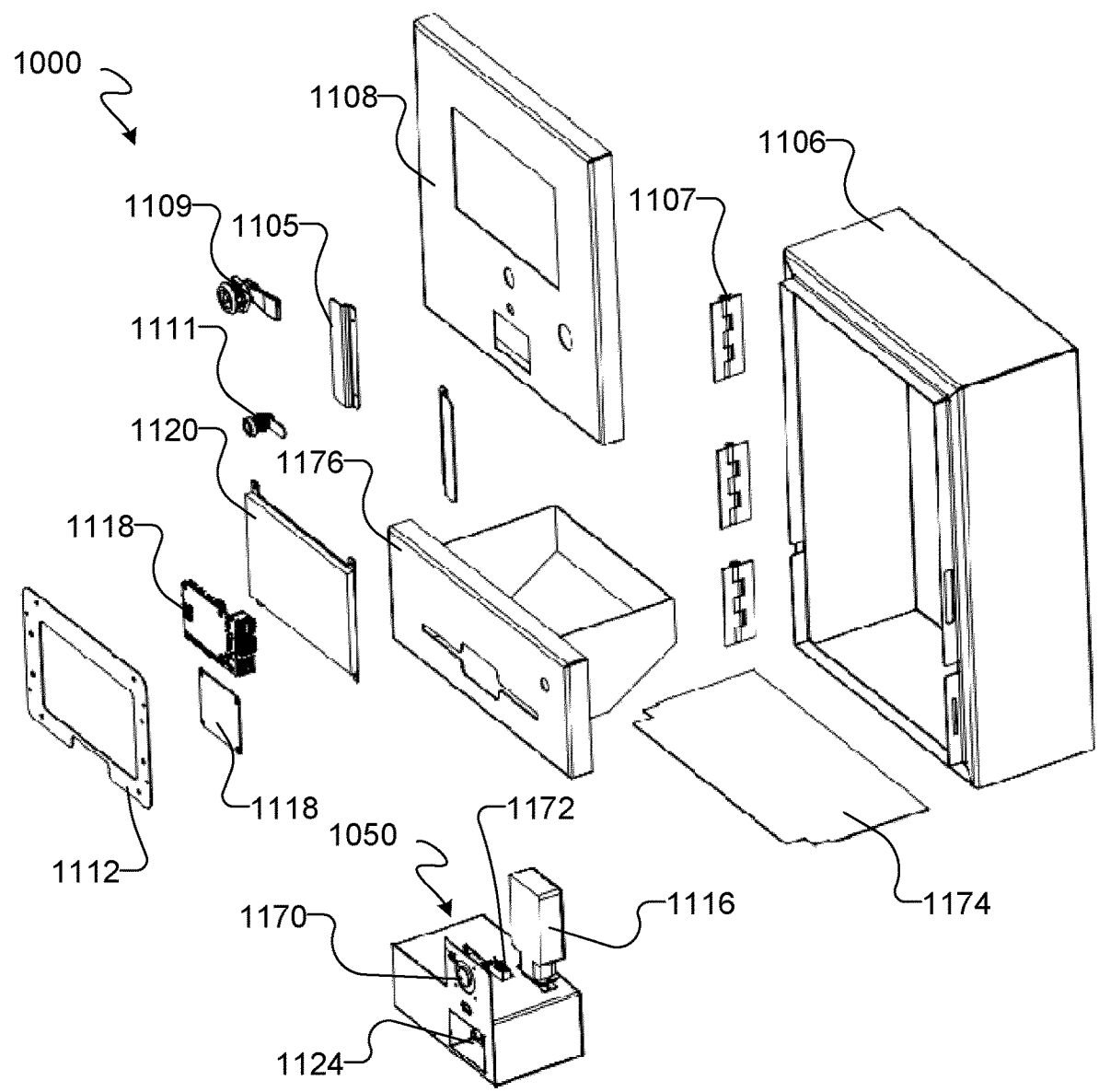
FIG. 8C shows an exploded view of the contact-free breath analysis apparatus.

With reference to FIG. 8C, apparatus 1000 has a rear housing 1106 and a front panel 1108 coupled together via hinges 1107. A door lock having two parts 1109 and 1111 is provided so that front panel 1108 can be locked to rear housing 1106 to prevent undesired entry into or interference with apparatus 1000. An LCD display module 1120 is provided to allow the output of results or commands to a user of apparatus 1000, and one or more printed circuit boards 1118 are provided to control the operation of apparatus 1000.

An analysis module comprising a pneumatic and sensor box 1050 is provided to carry out the breath analysis, and a replaceable sensor cartridge 1116 is provided as part of analysis module 1050. A camera 1170 is provided as part of apparatus 1000, and can be used to carry out a plurality of different functions such as user identification (e.g. via implementation of appropriate facial recognition technology), preservation of user identity (e.g. by taking a photograph of the subject using apparatus 1000), to assist in verifying the correct positioning of a subject using apparatus 1000 to deliver an acceptable sample, and so on.

A box electrical connector 1172 is provided on analysis module 1050, and is compatible with the corresponding connector (illustrated as 1119) provided on replaceable sensor cartridge 1116. An air inlet 1124 is also provided on analysis module 1050 for receiving the breath sample from a user of apparatus 1000. A box divider 1174 is provided for dividing the upper and lower portions of apparatus 1000. A front holding panel 1112 is provided for securing the components of apparatus 1000 in place and appropriate hinges 1105 can be used to allow access to various components of apparatus 1000 when in use.

Figure 8D:
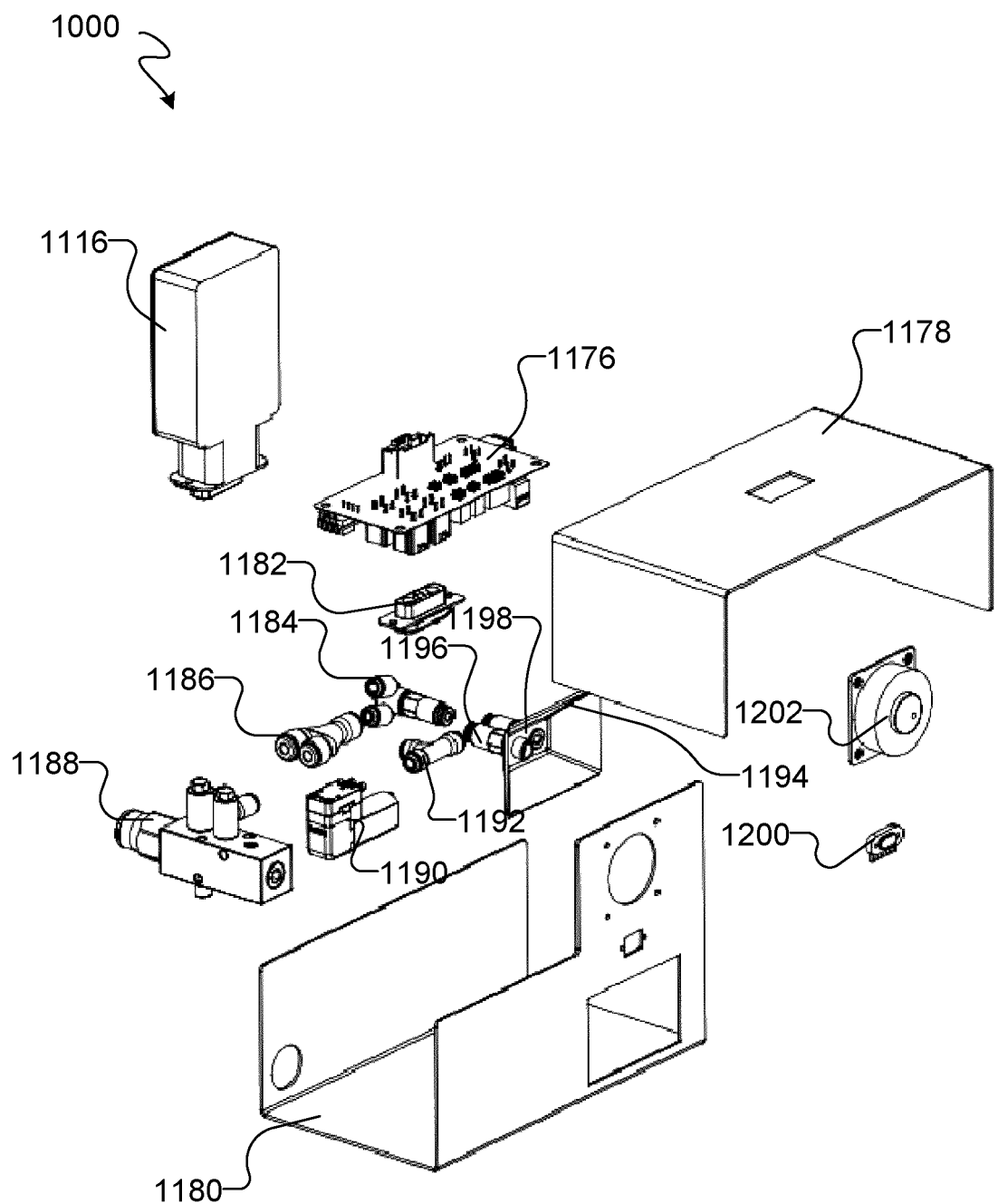
FIG. 8D is an exploded view thereof.

With reference to FIG. 8D, an interconnecting printed circuit board 1176 is provided for controlling the operation of apparatus 1000. A housing having a top panel 1178 and holder box 1180 is provided to contain components of the pneumatic circuit used to supply a user's breath sample to sensor cartridge 1116. An electrical connector 1182 is provided for engaging with replaceable sensor cartridge 1116, and two 3-way quick connect connectors 1184, 1186 are used to provide the pneumatic circuit to deliver a portion of a user's breath sample to replaceable sensor cartridge 1116 for analysis.

Figure 8E:
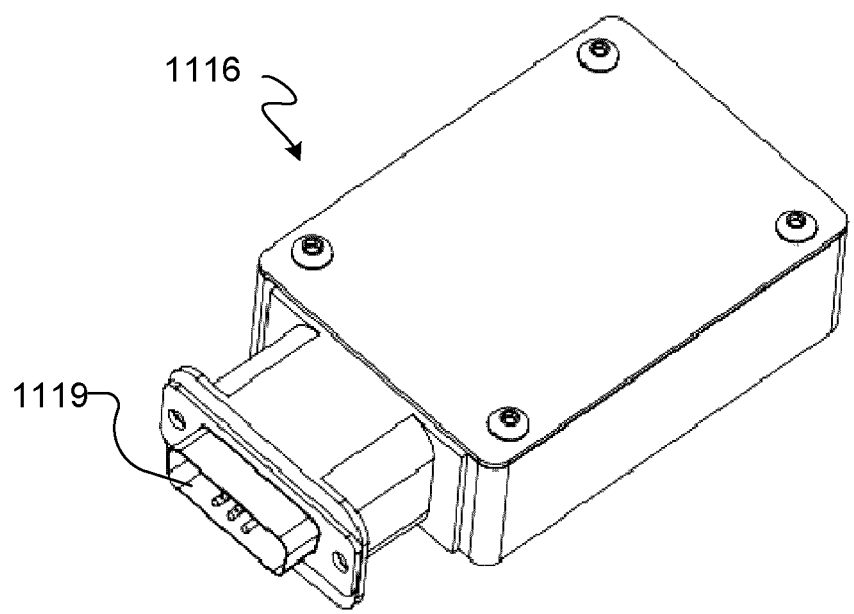
FIG. 8E is a perspective view of the replaceable sensor cartridge.
Figure 8F:
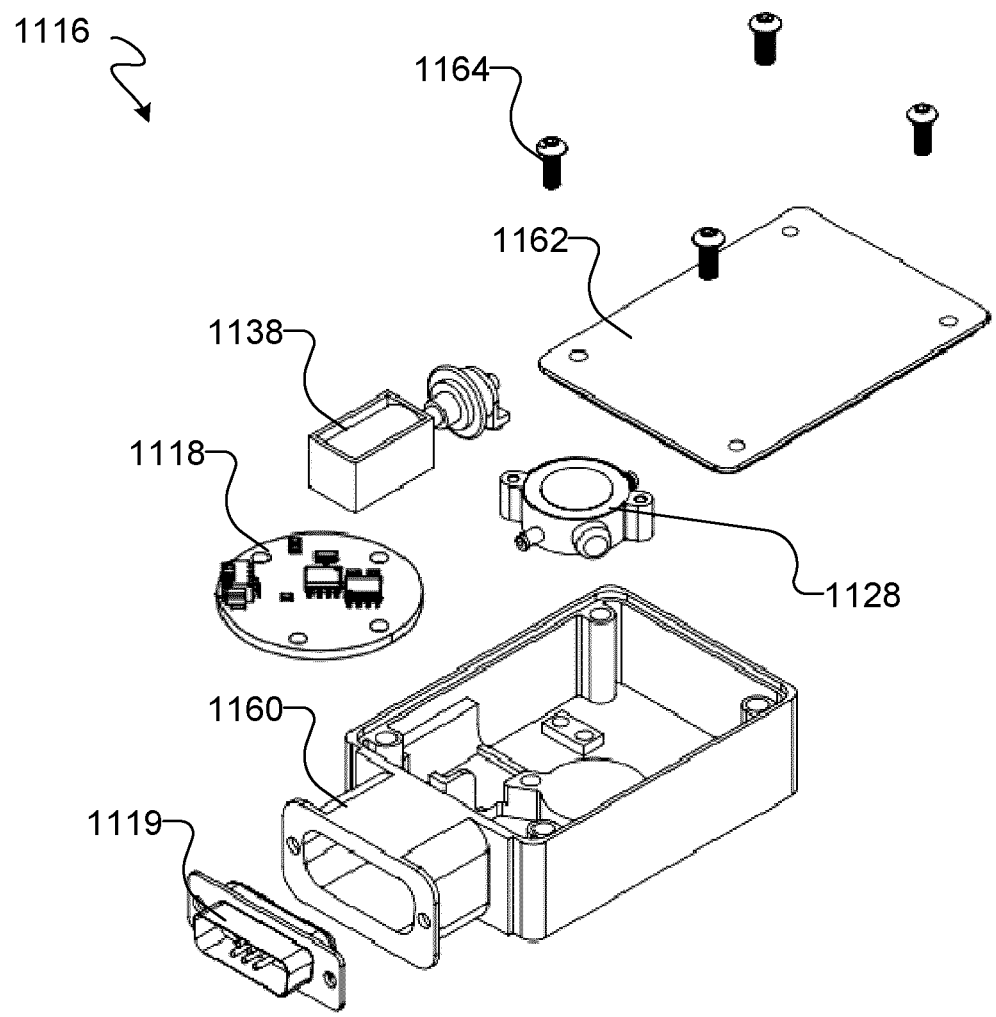
FIG. 8F is an exploded view thereof.

As best seen in FIGS. 8E and 8F, the replaceable sensor cartridge 1116 has an analyte sensor 1128, a sampling pump 1138, an exterior housing 1160 and removable panel 1162 couplable thereto (e.g. by fasteners such as screws 1164). A printed circuit board 1118 is provided to control the operation of sensor cartridge 1116, and a suitable electrical connector such as a D9 connector 1119 in the illustrated embodiment is provided to couple replaceable sensor cartridge 1116 to contact-free breath analysis apparatus 1000. An exhaust manifold 1188 is provided to exhaust excess breath from the pneumatic circuit.

Diaphragm pump 1190 is provided to draw a user's breath through the sampling arm of the pneumatic circuit, and a quick connect T-junction 1192 is also used as part of the pneumatic circuit. A front panel 1194 supports the breath sample inlet 1196 and the pressure sensor fluid flow path inlet 1198. A proximity sensor 1200 and camera 1202 are also provided to assist with establishing the proper positioning and/or identity of a user of apparatus 1000.

A straw container 1210 is provided to supply tubes or straws for users who elect to provide a breath sample using such apparatus, and includes an aperture 1212 through which the user can withdraw a tube to provide the breath sample.

Figure 9:
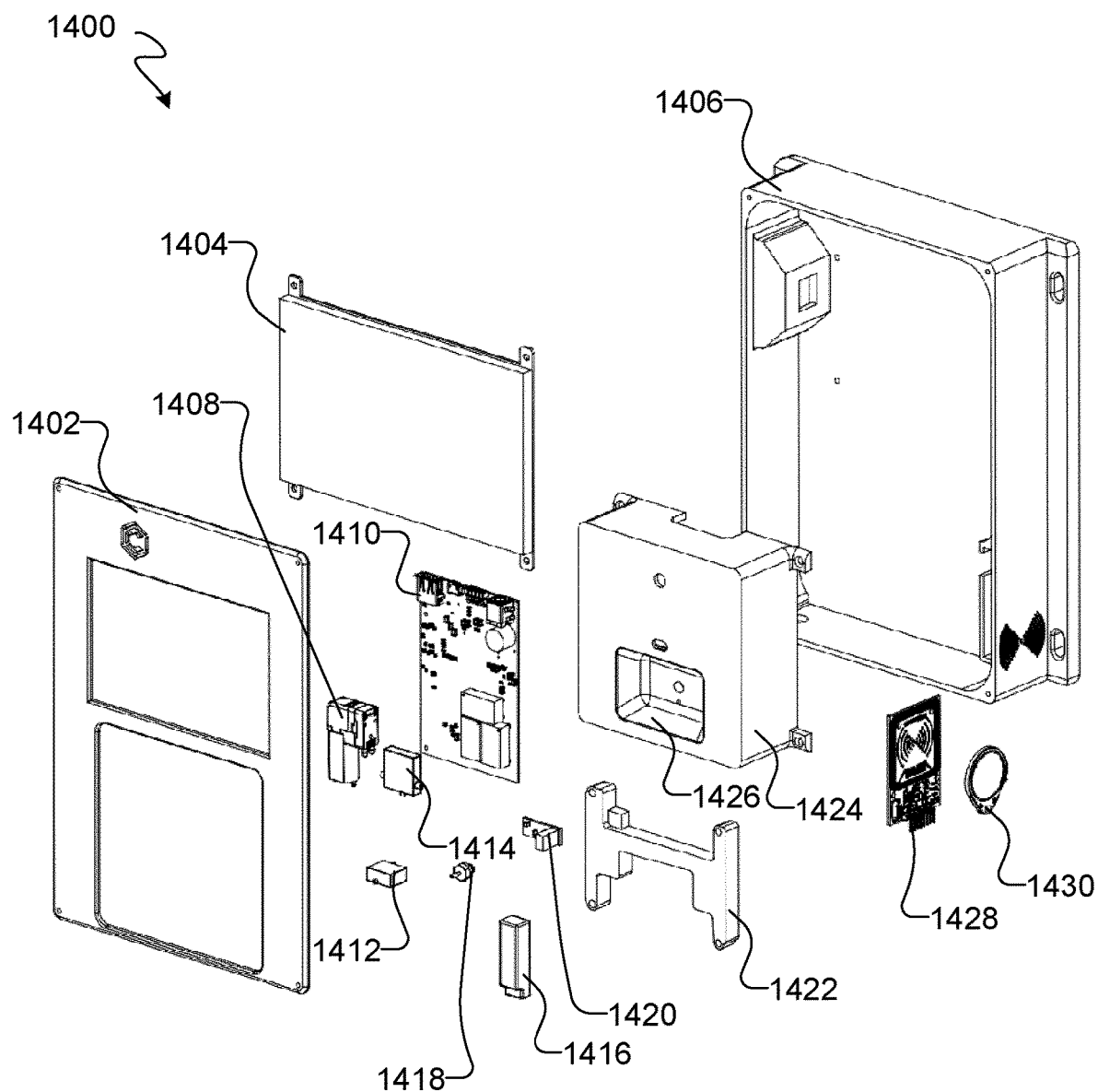
FIG. 9 shows a second example embodiment of a contact-free breath analysis apparatus that is mounted within a standalone cabinet.

In some embodiments, an RFID module is incorporated into the contact-free breath analysis apparatus, to allow for rapid identification of a user of the apparatus. Such an embodiment is illustrated with reference to FIG. 9 as breath analysis apparatus 1400. The components of apparatus 1400 can be similar to or the same as the components of apparatus 1000 with the addition of an RFID module. Apparatus 1400 has a front panel 1402, a capacitive touch screen 1404, a back panel 1406, a diaphragm pump 1408, a printed circuit board 1410, a pressure sensor 1412, an analyte sensor 1414, a sampling pump 1416, a nipple connector 1418 for supplying the breath sample to a pneumatic circuit, a proximity sensor 1420, a bracket or holder 1422, a front panel for defining inter alia the breath sample inlet cone 1426, and an RFID reader module 1428 for reading one or more RFID tags 1430.

While exemplary embodiments have been described herein with reference to the provision of a breath sample, including in a contact-free manner, other embodiments have applications for other purposes. Because a pump is used to draw an air sample into the device, alternative embodiments of the apparatus disclosed herein can be used as sniffers to passively monitor for specific desired analytes. For example, such apparatus can be disposed at a convenient point within a room and then monitor for the presence of specific analytes, including e.g. environmental contaminants or dust levels, by pumping air from the room into the apparatus for evaluation. Further, in embodiments incorporating an identification module such as a camera or an RFID module, the apparatus can be used to monitor attendance, e.g. at a workplace by employees, by having the employees regularly scan in and out or at scheduled times throughout the day while they are on the premises.

Further, apparatus according to various embodiments can be designed to incorporate appropriate data storage and/or communications facilities to allow results obtained by the apparatus to be reviewed. In some embodiments, a communications facility is provided so that data obtained by the apparatus can be uploaded to and/or information or instructions downloaded from a cloud computing facility. In some embodiments, the apparatus can provide notifications such as email or text notifications as results are obtained, and/or can create a log report or other desired report for review and use by an administrator.

While a number of exemplary aspects and embodiments have been discussed above, those of skill in the art will recognize certain modifications, permutations, additions and sub-combinations thereof. For example and without limitation:

Rather than being provided at an upstream end of main fluid flow path 746 as shown in FIG. 5, miniature diaphragm pump 736 can be positioned towards or at a downstream end of the main fluid flow path 746.

In some embodiments, the separation channel such as microfluidic channel 744 is omitted.

Carbon dioxide sensor 132 and temperature and/or humidity sensor 134 can be positioned at any desired location within the apparatus. By way of example only and without limitation, the positions of these sensors could be reversed in FIG. 5 so that carbon dioxide sensor 732 is located towards an upstream end of the apparatus (e.g. at inlet cone 724), and temperature and/or humidity sensor 734 is located towards a downstream end of the apparatus.

It is therefore intended that the following appended claims and claims hereafter introduced are interpreted to include all such modifications, permutations, additions and sub-combinations as are consistent with the broadest interpretation of the specification as a whole.

The invention claimed is:

1. An apparatus for evaluating a concentration of a target analyte in a user's bloodstream using a breath sample obtained in either a contact-free manner or using a mouthpiece, the apparatus comprising:
   first and second inlets for receiving a respective portion of the breath sample and directing the respective portion along separate first and second fluid flow paths, respectively, wherein, when the breath sample is provided in the contact-free manner, the respective portions of the breath sample are directed to both the first and second inlets, and when the breath sample is provided using the mouthpiece, the breath sample is directed to only the first inlet;
   an analyte sensor in fluid communication with the first inlet along a sampling arm of the first fluid flow path;
   a first pressure sensor in fluid communication with the second inlet along the second fluid flow path;
   a first pump positioned to draw a portion of the breath sample into the sampling arm of the first fluid flow path,
      wherein the first pump is configured to be activated when the first pressure sensor senses breath supplied through the second fluid flow path, and the first pump is configured to not be activated when breath is supplied through the first fluid flow path using the mouthpiece; and
   a second pump positioned to draw a portion of the breath sample to the analyte sensor from the sampling arm.

2. The apparatus as defined in claim 1, comprising a selectivity channel interposing the sampling arm and the analyte sensor.

3. The apparatus as defined in claim 2, wherein the selectivity channel comprises a microfluidic channel.

4. The apparatus as defined in claim 1, wherein the first inlet is configured to receive a sample tube.

5. The apparatus as defined in claim 1, comprising a second pressure sensor on the first fluid flow path.

6. The apparatus as defined in claim 5, wherein the first fluid flow path comprises the sampling arm and a regulating arm, the sampling arm and the regulating arm being separated by a T-connector, and wherein the second pressure sensor is provided on the regulating arm and the second pump is provided on the sampling arm.

7. The apparatus as defined in claim 6, wherein a one-way valve that allows only downstream flow of air interposes the second pressure sensor and the T-connector.

8. The apparatus as defined in claim 7, comprising an exhaust at a downstream end of the sampling arm and of the regulating arm.

9. The apparatus as defined in claim 1 wherein the analyte sensor and the second pump are provided in a replaceable sensor cartridge.

10. A cabinet-mounted unit, steering wheel or rearview mirror comprising the apparatus as defined in claim 1.

11. A method of evaluating a concentration of a target analyte in a first user's bloodstream using an apparatus allowing for collection of a breath sample in either a contact-free manner or using a mouthpiece, the method comprising:
   receiving the breath sample from the first user in the contact-free manner;
   directing the breath sample provided in the contact-free manner simultaneously through separate first and second fluid flow paths via first and second inlets;
   using a first pressure sensor in fluid communication with the second inlet to activate a first pump positioned to draw a portion of the breath sample into a sampling arm of the first fluid flow path;
   using a second pump to draw a portion of the breath sample from the sampling arm to the analyte sensor; and
   evaluating the concentration of the target analyte in the user's bloodstream using an analyte sensor, the analyte sensor being in fluid communication with the first fluid flow path,
   wherein, when the breath sample is provided using the mouthpiece, the breath sample is directed to only the first inlet, and the first pump is not activated.

12. The method as defined in claim 11, further comprising using the first pressure sensor to calculate a volume of the provided breath sample.

13. The method as defined in claim 12, wherein the steps of using the second pump to draw the portion of the breath sample from the sampling arm to the analyte sensor and using the analyte sensor are carried out on a replaceable sensor cartridge.

14. The method as defined in claim 11, wherein the first fluid flow path comprises the sampling arm and a regulating arm, the sampling arm and the regulating arm being separated by a T-connector, wherein the regulating arm comprises a one-way valve that allows the breath sample to flow only in a downstream direction, the method comprising using the one-way valve to prevent upstream flow of fluid through the regulating arm.

15. The method as defined in claim 14, further comprising receiving a second breath sample from a second user via a sample tube coupled to the first inlet.

16. The method as defined in claim 15, further comprising using a second pressure sensor disposed on the first fluid flow path to calculate a volume of the second breath sample.

17. The method as defined in claim 16, wherein the second pressure sensor is disposed on the regulating arm downstream of the one-way valve, the method comprising allowing pressure of the second user's breath sample to open the one-way valve.

18. The method as defined in claim 15, comprising allowing the first or second user's breath sample to exit the first fluid flow path through an exhaust.

19. The method as defined in claim 11, comprising using the first pump to purge the analyte sensor after a breath sample has been provided.

* * * * *